(12) United States Patent
Santini, Jr. et al.

(10) Patent No.: US 7,892,221 B2
(45) Date of Patent: *Feb. 22, 2011

(54) METHOD OF CONTROLLED DRUG DELIVERY FROM IMPLANT DEVICE

(75) Inventors: John T. Santini, Jr., Chelmsford, MA (US); Michael J. Cima, Winchester, MA (US); Robert S. Langer, Newton, MA (US); Achim Göpferich, Sinzing (DE)

(73) Assignee: Massachusetts Institute of Technology, Cambridge, MA (US)

( * ) Notice: Subject to any disclaimer, the term of this patent is extended or adjusted under 35 U.S.C. 154(b) by 1604 days.

This patent is subject to a terminal disclaimer.

(21) Appl. No.: 11/041,161

(22) Filed: Jan. 21, 2005

(65) Prior Publication Data

US 2005/0149000 A1 Jul. 7, 2005

Related U.S. Application Data

(63) Continuation of application No. 09/665,303, filed on Sep. 19, 2000, now Pat. No. 7,070,590, which is a continuation-in-part of application No. 09/022,322, filed on Feb. 11, 1998, now Pat. No. 6,123,861, which is a continuation-in-part of application No. 08/675,375, filed on Jul. 2, 1996, now Pat. No. 5,797,898.

(51) Int. Cl.
*A61K 9/22* (2006.01)
(52) U.S. Cl. .................. 604/890.1; 604/93.01
(58) Field of Classification Search ............ 604/891, 604/891.1, 20, 93.01, 288.01; 128/899
See application file for complete search history.

(56) References Cited

U.S. PATENT DOCUMENTS 3,692,027 A 9/1972 Ellinwood, Jr.
3,921,636 A 11/1975 Zaffaroni (Continued)

FOREIGN PATENT DOCUMENTS

DE 296 998 A5 7/1988

(Continued)

OTHER PUBLICATIONS

Armani, et al., "Microfabrication Technology for Polycaprolactone, a Biodegradable Polymer," *J. Micromech. Microeng.* 10:80-84 (2000).

(Continued)

*Primary Examiner*—Nicholas D Lucchesi
*Assistant Examiner*—Quynh-Nhu H Vu
(74) *Attorney, Agent, or Firm*—Sutherland Asbill & Brennan LLP

(57) ABSTRACT

Reservoir-based medical devices are provided. In one embodiment, the medical device comprises a substrate; at least two discrete, microfabricated reservoirs provided in spaced positions across at least one surface of the substrate; discrete reservoir caps covering the at least two reservoirs; and control circuitry for selectively disintegrating the reservoir caps to open the reservoirs. The reservoirs of the device can include a diagnostic reagent or other molecules useful in medical diagnostics. In one embodiment, the reservoir cap comprises an anode and the control circuitry comprises a cathode and a power source for creating an electric potential between the cathode and the anode. Application of the electric potential causes the reservoir cap to disintegrate, thereby opening the reservoir.

23 Claims, 9 Drawing Sheets

U.S. PATENT DOCUMENTS

| | | | |
|---|---|---|---|
| 3,952,741 A | 4/1976 | Baker | |
| 3,976,983 A | 8/1976 | Moussie | |
| 4,003,379 A | 1/1977 | Ellinwood, Jr. | |
| 4,089,734 A | 5/1978 | Bierig | |
| 4,146,029 A | 3/1979 | Ellinwood, Jr. | |
| 4,209,894 A | 7/1980 | Keen | |
| 4,345,981 A | 8/1982 | Bennett et al. | |
| 4,360,019 A | 11/1982 | Portner et al. | |
| 4,507,115 A | 3/1985 | Kambara et al. | |
| 4,585,652 A | 4/1986 | Miller et al. | |
| 4,731,049 A | 3/1988 | Parsi | |
| 4,731,051 A | 3/1988 | Fishell | |
| 4,793,825 A | 12/1988 | Benjamin et al. | |
| 4,874,500 A | 10/1989 | Madou | |
| 4,919,666 A | 4/1990 | Buchhorn | |
| 4,994,023 A | 2/1991 | Wellinghoff et al. | |
| 5,041,107 A | 8/1991 | Heil, Jr. | |
| 5,042,975 A | 8/1991 | Chien et al. | |
| 5,102,402 A | 4/1992 | Dror et al. | |
| 5,167,625 A | 12/1992 | Jacobsen et al. | |
| 5,170,801 A | 12/1992 | Casper et al. | |
| 5,196,002 A | 3/1993 | Hanover et al. | |
| 5,200,051 A | 4/1993 | Cozzette et al. | |
| 5,252,294 A | 10/1993 | Kroy et al. | |
| 5,254,081 A | 10/1993 | Maurer et al. | |
| 5,279,607 A | 1/1994 | Schentag et al. | |
| 5,288,504 A | 2/1994 | Versic | |
| 5,304,293 A | 4/1994 | Tierney et al. | |
| 5,318,557 A | 6/1994 | Gross | |
| 5,336,213 A | 8/1994 | D'Angelo et al. | |
| 5,366,454 A * | 11/1994 | Currie et al. | 604/890.1 |
| 5,368,588 A | 11/1994 | Bettinger | |
| 5,368,704 A | 11/1994 | Madou et al. | |
| 5,380,272 A | 1/1995 | Gross | |
| 5,387,419 A | 2/1995 | Levy et al. | |
| 5,425,710 A | 6/1995 | Khair et al. | |
| 5,427,585 A | 6/1995 | Bettinger | |
| 5,429,822 A | 7/1995 | Gresser et al. | |
| 5,443,508 A | 8/1995 | Giampapa | |
| 5,449,382 A | 9/1995 | Dayton | |
| 5,474,527 A | 12/1995 | Bettinger | |
| 5,490,962 A * | 2/1996 | Cima et al. | 264/401 |
| 5,518,680 A | 5/1996 | Cima et al. | |
| 5,533,995 A | 7/1996 | Corish et al. | |
| 5,547,470 A | 8/1996 | Johnson et al. | |
| 5,605,662 A | 2/1997 | Heller et al. | |
| 5,609,629 A | 3/1997 | Fearnot et al. | |
| 5,648,399 A * | 7/1997 | Friedman et al. | 514/772.6 |
| 5,651,900 A | 7/1997 | Keller et al. | |
| 5,660,680 A | 8/1997 | Keller | |
| 5,707,385 A | 1/1998 | Williams | |
| 5,769,884 A | 6/1998 | Solovay | |
| 5,770,076 A | 6/1998 | Chu et al. | |
| 5,782,799 A | 7/1998 | Jacobsen et al. | |
| 5,797,898 A | 8/1998 | Santini, Jr. et al. | |
| 5,798,042 A | 8/1998 | Chu et al. | |
| 5,824,049 A | 10/1998 | Ragheb et al. | |
| 5,824,204 A | 10/1998 | Jerman | |
| 5,830,659 A | 11/1998 | Stewart | |
| 5,842,787 A | 12/1998 | Kopf-Sill et al. | |
| 5,843,172 A | 12/1998 | Yan | |
| 5,843,767 A | 12/1998 | Beattie | |
| 5,863,708 A | 1/1999 | Zanzucchi et al. | |
| 5,873,904 A | 2/1999 | Ragheb et al. | |
| 5,879,697 A | 3/1999 | Ding et al. | |
| 5,891,108 A | 4/1999 | Leone et al. | |
| 5,893,840 A | 4/1999 | Hull et al. | |
| 5,893,974 A | 4/1999 | Keller et al. | |
| 5,900,160 A | 5/1999 | Whitesides et al. | |
| 5,938,923 A | 8/1999 | Tu et al. | |
| 5,947,893 A | 9/1999 | Agrawal | |
| 5,948,255 A | 9/1999 | Keller et al. | |
| 5,951,881 A | 9/1999 | Rogers et al. | |
| 5,962,081 A | 10/1999 | Öhman et al. | |
| 5,972,027 A | 10/1999 | Johnson | |
| 5,985,328 A | 11/1999 | Chu et al. | |
| 5,989,445 A | 11/1999 | Wise et al. | |
| 6,001,090 A | 12/1999 | Lenhart | |
| 6,027,695 A | 2/2000 | Oldenburg et al. | |
| 6,042,875 A | 3/2000 | Ding et al. | |
| 6,056,734 A | 5/2000 | Jacobsen et al. | |
| 6,062,461 A | 5/2000 | Sparks et al. | |
| 6,068,752 A | 5/2000 | Dubrow et al. | |
| 6,071,305 A | 6/2000 | Brown et al. | |
| 6,096,070 A | 8/2000 | Ragheb et al. | |
| 6,099,561 A | 8/2000 | Alt | |
| 6,114,658 A | 9/2000 | Roth et al. | |
| 6,123,861 A | 9/2000 | Santini, Jr. et al. | |
| 6,129,705 A | 10/2000 | Grantz | |
| 6,136,212 A | 10/2000 | Mastrangelo et al. | |
| 6,140,740 A | 10/2000 | Porat et al. | |
| 6,163,720 A | 12/2000 | Gyory et al. | |
| 6,171,850 B1 | 1/2001 | Nagle et al. | |
| 6,197,013 B1 | 3/2001 | Reed et al. | |
| 6,241,762 B1 | 6/2001 | Shanley | |
| 6,245,104 B1 | 6/2001 | Alt | |
| 6,253,443 B1 | 7/2001 | Johnson | |
| 6,261,584 B1 | 7/2001 | Peery et al. | |
| 6,273,908 B1 | 8/2001 | Ndondo-Lay | |
| 6,273,913 B1 | 8/2001 | Wright et al. | |
| 6,287,628 B1 | 9/2001 | Hossainy et al. | |
| 6,293,967 B1 | 9/2001 | Shanley | |
| 6,331,439 B1 | 12/2001 | Cherukui et al. | |
| 6,334,856 B1 | 1/2002 | Allen et al. | |
| 6,334,859 B1 | 1/2002 | Richter | |
| 6,349,232 B1 | 2/2002 | Gordon | |
| 6,361,522 B1 | 3/2002 | Scheiner et al. | |
| 6,364,856 B1 | 4/2002 | Ding et al. | |
| 6,378,292 B1 | 4/2002 | Youngner | |
| 6,379,382 B1 | 4/2002 | Yang | |
| 6,387,121 B1 | 5/2002 | Alt | |
| 6,391,052 B2 | 5/2002 | Buirge et al. | |
| 6,395,326 B1 | 5/2002 | Castro et al. | |
| 6,403,403 B1 | 6/2002 | Mayer et al. | |
| 6,437,640 B1 | 8/2002 | Mayer et al. | |
| 6,471,980 B2 | 10/2002 | Sirhan et al. | |
| 6,483,368 B2 | 11/2002 | Mayer et al. | |
| 6,491,666 B1 | 12/2002 | Santini, Jr. et al. | |
| 6,527,762 B1 | 3/2003 | Santini, Jr. et al. | |
| 6,527,799 B2 | 3/2003 | Shanley | |
| 6,530,951 B1 | 3/2003 | Bates et al. | |
| 6,537,250 B1 | 3/2003 | Kriesel | |
| 6,537,256 B2 | 3/2003 | Santini, Jr. et al. | |
| 6,551,838 B2 | 4/2003 | Santini, Jr. et al. | |
| 6,558,422 B1 | 5/2003 | Baker et al. | |
| 6,562,065 B1 | 5/2003 | Shanley | |
| 6,571,125 B2 | 5/2003 | Thompson | |
| 6,585,764 B2 | 7/2003 | Wright et al. | |
| 6,596,296 B1 | 7/2003 | Nelson et al. | |
| 6,638,302 B1 | 10/2003 | Curcio et al. | |
| 6,652,582 B1 | 11/2003 | Stinson | |
| 6,656,162 B2 * | 12/2003 | Santini et al. | 604/191 |
| 6,663,615 B1 | 12/2003 | Madou et al. | |
| 6,669,683 B2 | 12/2003 | Santini, Jr. et al. | |
| 6,679,911 B2 | 1/2004 | Burgermeister | |
| 6,699,281 B2 | 3/2004 | Vallana et al. | |
| 6,709,379 B1 | 3/2004 | Brandau et al. | |
| 6,764,507 B2 | 7/2004 | Shanley et al. | |
| 6,783,543 B2 | 8/2004 | Jang | |
| 6,916,483 B2 | 7/2005 | Ralph et al. | |
| 7,052,488 B2 * | 5/2006 | Uhland | 604/891.1 |
| 7,070,590 B1 * | 7/2006 | Santini et al. | 604/890.1 |
| 7,070,592 B2 * | 7/2006 | Santini et al. | 604/891.1 |
| 7,114,312 B2 * | 10/2006 | Coppeta et al. | 53/471 |

| | | | |
|---|---|---|---|
| 2001/0020151 A1 | 9/2001 | Reed et al. | |
| 2001/0027340 A1 | 10/2001 | Wright et al. | |
| 2001/0029660 A1 | 10/2001 | Johnson | |
| 2001/0034550 A1 | 10/2001 | Buirge et al. | |
| 2002/0007214 A1 | 1/2002 | Falotico | |
| 2002/0007215 A1 | 1/2002 | Falotico et al. | |
| 2002/0022826 A1 | 2/2002 | Reynolds et al. | |
| 2002/0038146 A1 | 3/2002 | Harry | |
| 2002/0072734 A1 | 6/2002 | Liedtke | |
| 2002/0072784 A1 | 6/2002 | Sheppard, Jr. et al. | |
| 2002/0082677 A1 | 6/2002 | Sirhan et al. | |
| 2002/0082678 A1 | 6/2002 | Sirhan et al. | |
| 2002/0082680 A1 | 6/2002 | Shanley et al. | |
| 2002/0099359 A1 | 7/2002 | Santini, Jr. et al. | |
| 2002/0107470 A1 | 8/2002 | Richards et al. | |
| 2002/0119176 A1 | 8/2002 | Greenberg et al. | |
| 2002/0138067 A1 | 9/2002 | Sheppard, Jr. et al. | |
| 2002/0151776 A1 | 10/2002 | Shawgo et al. | |
| 2002/0183721 A1 | 12/2002 | Santini, Jr. et al. | |
| 2002/0187260 A1 | 12/2002 | Sheppard, Jr. et al. | |
| 2002/0188282 A1 | 12/2002 | Greenberg | |
| 2003/0010808 A1 | 1/2003 | Uhland et al. | |
| 2003/0017190 A1 | 1/2003 | Sirhan et al. | |
| 2003/0028243 A1 | 2/2003 | Bates et al. | |
| 2003/0032946 A1 | 2/2003 | Fishman | |
| 2003/0036794 A1 | 2/2003 | Ragheb et al. | |
| 2003/0068355 A1 | 4/2003 | Shanley et al. | |
| 2003/0069560 A1 | 4/2003 | Adamis et al. | |
| 2003/0104590 A1 | 6/2003 | Santini, Jr. et al. | |
| 2003/0105455 A1 | 6/2003 | Santini, Jr. et al. | |
| 2003/0105511 A1 | 6/2003 | Welsh et al. | |
| 2003/0108659 A1 | 6/2003 | Bales | |
| 2003/0176854 A1 | 9/2003 | Rodstrom | |
| 2003/0176915 A1 | 9/2003 | Wright et al. | |
| 2003/0199970 A1 | 10/2003 | Shanley | |
| 2004/0034332 A1 | 2/2004 | Uhland et al. | |
| 2004/0121486 A1 | 6/2004 | Uhland et al. | |
| 2004/0122506 A1 | 6/2004 | Shanley et al. | |
| 2004/0143321 A1 | 7/2004 | Litvack et al. | |
| 2004/0143322 A1 | 7/2004 | Litvack et al. | |
| 2004/0225350 A1 | 11/2004 | Shanley | |
| 2004/0236408 A1 | 11/2004 | Shanley | |
| 2004/0243241 A1 | 12/2004 | Istephanous | |
| 2004/0254635 A1 | 12/2004 | Shanley et al. | |
| 2005/0055080 A1 | 3/2005 | Istephanous | |
| 2005/0203608 A1 | 9/2005 | Shanley | |
| 2005/0203609 A1 | 9/2005 | Shanley | |
| 2005/0260247 A1 | 11/2005 | Ralph et al. | |
| 2006/0246103 A1 | 11/2006 | Ralph et al. | |

FOREIGN PATENT DOCUMENTS

| | | |
|---|---|---|
| DE | 39 08 822 A1 | 3/1989 |
| DE | 197 16 683 C1 | 6/1998 |
| DE | 19716683 C1 | 6/1998 |
| EP | 0747069 A2 | 11/1996 |
| EP | 0832655 A2 | 1/1998 |
| EP | 0850604 A2 | 1/1998 |
| EP | 0875218 A2 | 11/1998 |
| EP | 0879595 A2 | 11/1998 |
| EP | 1358859 A1 | 5/2003 |
| FR | 2715568 A1 | 4/1995 |
| WO | 93/03790 | 3/1993 |
| WO | WO 93/03790 | 3/1993 |
| WO | WO 95/24472 | 9/1995 |
| WO | WO 96/40420 | 12/1996 |
| WO | WO 97/34697 | 9/1997 |
| WO | WO 97/47370 | 12/1997 |
| WO | 98/00107 | 1/1998 |
| WO | WO 98/00107 | 1/1998 |
| WO | 98/26814 | 6/1998 |
| WO | WO 98/23228 | 6/1998 |
| WO | WO 98/26814 | 6/1998 |
| WO | WO 98/46325 | 10/1998 |
| WO | WO 99/16500 | 4/1999 |
| WO | WO 99/55396 | 11/1999 |
| WO | 0135928 A1 | 5/2001 |
| WO | 0178798 A1 | 10/2001 |
| WO | WO 02/056862 A2 | 7/2002 |
| WO | WO 02/058678 A2 | 8/2002 |
| WO | 03028579 A1 | 4/2003 |
| WO | 03105710 A2 | 12/2003 |

OTHER PUBLICATIONS

Bae, et al., "Pulsatile Drug Release by Electric Stimulus," ACS Symp. Series *Polymeric Drugs & Drug Admin.*, pp. 99-110 (1994).

Bates, et al., "New Amorphous Thin-Film Lithium Electrolyte and Rechargeable Microbattery," *IEEE 35th International Power Sources Symposium.* pp. 337-339 (1992).

Bhattacharya, et al., "Next Generation Integral Passives: Materials, Processes, and Integration of and Capacitors on PWB Substrates," *J. Mater. Sci.-Mater. Electron.* 11(3):253-68 (2000).

Cheng, et al., "Localized Silicon Fusion and Eutectic Bonding for MEMS Fabrication and Packaging," *J. Microelectromechanical Syst.* 9:3-8 (2000).

Ehrick, et al., "Artificial Muscle-Based Microactuators for Reversible Controlled Release," ACS Abstracts, No. 22, 222nd ACS Nat'l Meeting (Chicago, 2001) (abstract).

Haroun, et al., "Local Drug Delivery," *Curr. Opin. Oncol.* 12(3): 187-93 (2000) (abstract).

Jaeger, "Introduction to Microelectronic Fabrication" *Modular Series on Solid State Devices*, vol. 5. (1988).

Jones, et al., "Development and Performance of a Rechargeable Thin-Film Solid-State Microbattery," *J. Power Sources.* 54:63-67 (1995).

Kwon, et al., "Electrically Erodible Polymer Gel for Controlled Release of Drugs," *Nature* 354:291-293 (1991).

Low, et al., "Microactuators Towards Microvalves for Responsive Controlled Drug Delivery," *Sensors & Actuators B* 67: 149-60 (2000).

Madou, et al., "From Batch to Continuous Manufacturing of Microbiomedical Devices," *Chem. Rev.*, 100: 2679-92 (2000).

Madou, *Fundamentals of Microfabrication*, pp. 468-512 (CRC Press 1997).

Madou, et al., "Exploitation of a Novel Artificial Muscle for Controlled Drug Delivery," pp. 495-497 (1999).

Santini Jr., et al., "Microchips as Controlled Drug-Delivery Devices," *Angew Chem. Int. Ed. Engl.* 39(14): 2396-407 (2000).

Santini Jr., et al., "Microchip Technology in Drug Delivery," *Ann. Med.* 32(6) 377-79 (2001).

Santini Jr., et al., "A Controlled-Release Microchip," *Nature* 397(6717): 335-38 (1999).

Surbled, et al., "Characterization of Sputtered TiNi Shape Memory Alloy Thin Films," *Jpn. J. Appl. Phys.* 38: L1547-L1549 (1999).

Surbled, et al., "Shape Memory Alloys for Micromembranes Actuation," *SPIE.* 3825: 63-70 (1999).

Surbled, et al., "Array of Shape Memory Alloy One-Shot Micro-Valves for Drug Delivery," MME '99, Gif sur Yvette, France (Sep. 27-28, 1999).

Tao, et al., "Microfabricated Drug Delivery Systems: From Particles to Pores," *Adv. Drug Deliv. Res.* 55(3): 315-28 (2003).

Tierney, et al.; "New Electrorelease Systems Based on Microporous Membranes," *J. Electrochem. Soc.*, 137:3789-3793 (1990).

Tierney, et al., "Electroreleasing Composite Membranes for Delivery of Insulin and Other Biomacromolecules," *J. Electrochem. Soc.*, 137:2005-2006 (1990).

Uhrich, et al., "Synethsis and Characterization of Degradable Poly(anhydride-co-imides)," *Macromolecules* 28:2184-2193 (1995).

Vladimirsky, et al., "Thin Metal Film Thermal Micro-Sensors," *Proc. SPIE-Int. Soc. Opt. Eng.* 2640:184-92 (1995).

Wogersien, et al., "Fabrication of Thin Film Resistors and Silicon Microstructures Using a Frequency Doubled Nd:YAG-Laser," *Proc. SPIE-Int. Soc. Opt. Eng.* 3680:1105-12 (1999).

Wolf, et al., "Silicon Processing for the VLSI Era," *Process Technology.* vol. 1. (1986).

Yao, et al., "Low Temperature Eutectic Bonding for In-Plane Type Micro Thermoelectric Cooler," *Proc. ASME Intl. Mech. Eng. Congr. & Expo* (2001).

Kwon, et al., "Electrically Erodible Polymer Gel for Controlled Release of Drugs," Nature 354:291-93 (1991).

Low, et al., "Microactuators Towards Microvalves for Responsive Controlled Drug Delivery," Sensors & Actuators B 67: 149-60 (2000).

Madou et al., "From Batch to Continuous Manufacturing of Microbiomedical Devices," Chem. Rev., 100: 2679-92 (2000).

Madou et al., "Exploitation of a Novel Artificial Muscle for Controlled Drug Delivery," pp. 495-497 (1999).

Tierney, et al., "New Electrorelease Systems Based on Microporous Membranes," J. Electrochem. Soc., 137:3789-93 (1990).

Tierney, et al., "Electroreleasing Composite Membranes for Delivery of Insulin and Other Biomacromolecules," J. Electrochem. Soc., 137:2005-06 (1990).

Uhrich, et al., "Synthesis and Characterization of Degradable Poly(anhydride-co-imides)," Macromolecules 28:2184-93 (1995).

\* cited by examiner

- ▨ RELEASE SYSTEM CONTAINING THE DRUG OR OTHER MOLECULE
- ▨ ANODE AND CATHODE MATERIAL
- ▨ INSULATOR OVERLAYER AND ETCH MASK MATERIAL

 DEGRADABLE RESERVOIR CAP MATERIAL
 NON-DEGRADABLE RESERVOIR-CAP MATERIAL
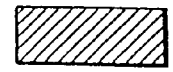 DEGRADABLE RELEASE SYSTEM
 NON-DEGRADABLE RELEASE SYSTEM
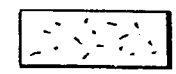 PURE DRUG OR OTHER MOLECULE (SOLID, LIQUID, OR GEL FORM)
 INSULATOR/ETCH MASK MATERIAL

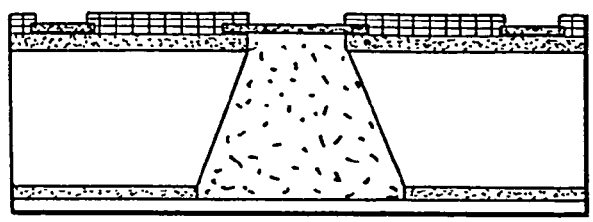
FIG. 8a
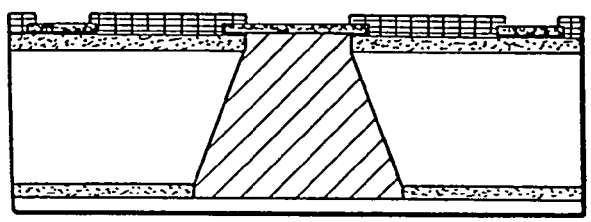
FIG. 8b
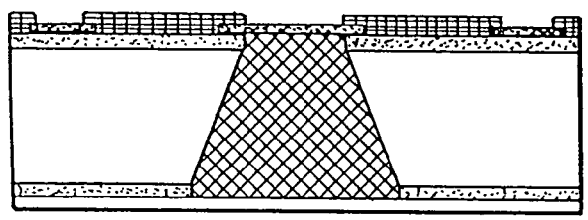
FIG. 8c
 INSULATOR / ETCH MASK MATERIAL
 ANODE AND CATHODE MATERIAL
 INSULATOR OVERLAYER
 DEGRADABLE RELEASE SYSTEM
 NON-DEGRADABLE RELEASE SYSTEM
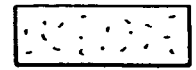 PURE DRUG OR OTHER MOLECULE (SOLID, LIQUID, OR GEL FORM)

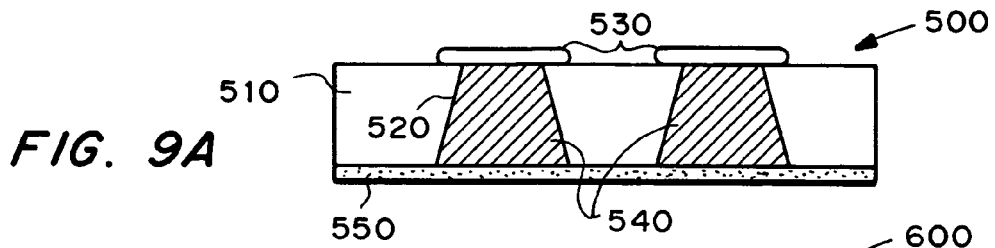
*FIG. 9A*
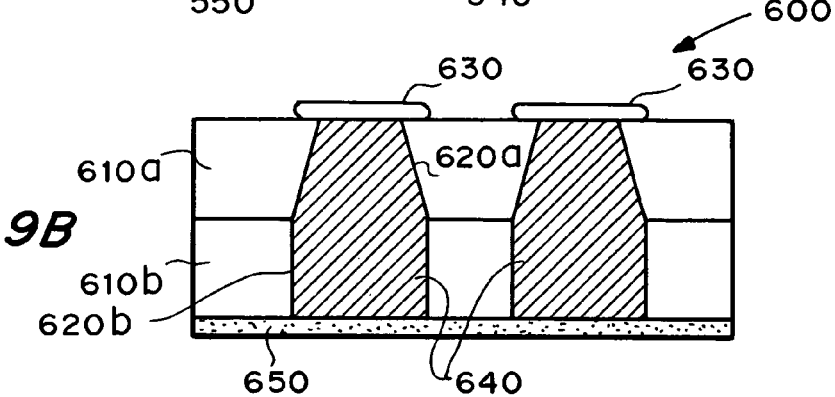
*FIG. 9B*
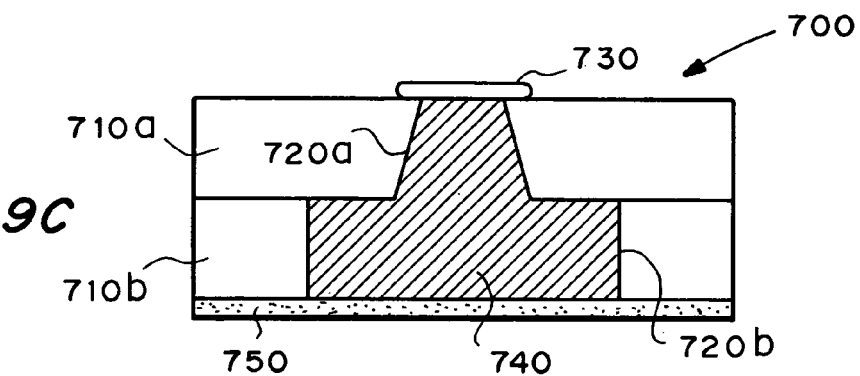
*FIG. 9C*
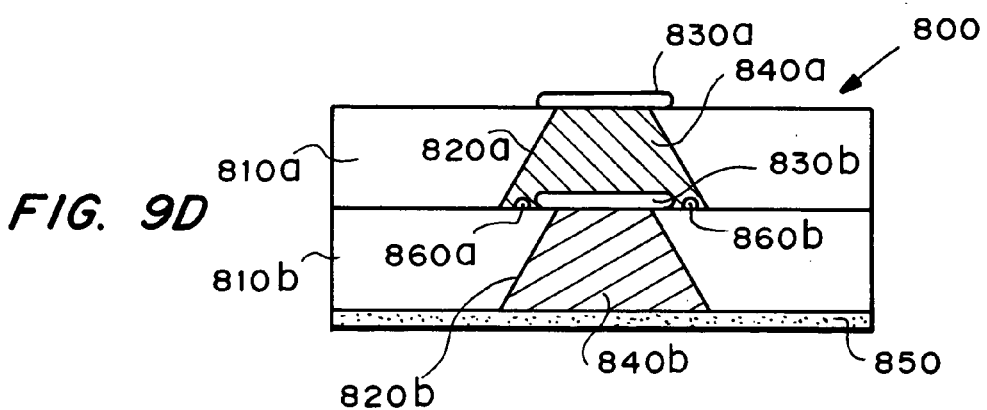
*FIG. 9D*
*FIG. 9E*
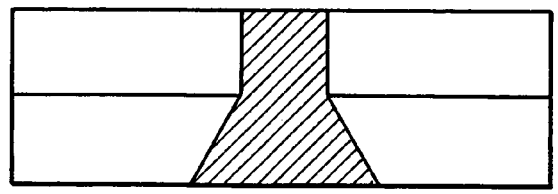

METHOD OF CONTROLLED DRUG DELIVERY FROM IMPLANT DEVICE

CROSS-REFERENCE TO RELATED APPLICATIONS

This is a continuation of U.S. application Ser. No. 09/665,303, filed Sep. 19, 2000, now U.S. Pat. No. 7,070,590 which is a continuation-in-part of U.S. application Ser. No. 09/022,322, filed Feb. 11, 1998, now U.S. Pat. No. 6,123,861, which is a continuation-in-part of U.S. application Ser. No. 08/675,375, filed Jul. 2, 1996, now U.S. Pat. No. 5,797,898. These applications are incorporated herein by reference in their entirety.

BACKGROUND OF THE INVENTION

This invention relates to miniaturized drug delivery devices and more particularly, to controlled time and rate release multi-welled drug delivery devices.

Drug delivery is an important aspect of medical treatment. The efficacy of many drugs is directly related to the way in which they are administered. Some therapies require that the drug be repeatedly administered to the patient over a long period of time. This makes the selection of a proper drug delivery method problematic. Patients often forget, are unwilling, or are unable to take their medication. Drug delivery also becomes problematic when the drugs are too potent for systemic delivery. Therefore, attempts have been made to design and fabricate a delivery device which is capable of the controlled, pulsatile or continuous release of a wide variety of molecules including, but not limited to, drugs and other therapeutics.

Controlled release polymeric devices have been designed to provide drug release over a period of time via diffusion of the drug out of the polymer and/or degradation of the polymer over the desired time period following administration to the patient. However, these devices are relatively simple.

U.S. Pat. No. 5,490,962 to Cima, et al. discloses the use of three dimensional printing methods to make more complex devices which provide release over a desired time frame, of one or more drugs. Although the general procedure for making a complex device is described, specific designs are not detailed.

U.S. Pat. No. 4,003,379 to Ellinwood describes an implantable electromechanically driven device that includes a flexible retractable walled container, which receives medication from a storage area via an inlet and then dispenses the medication into the body via an outlet. U.S. Pat. Nos. 4,146,029 and 3,692,027 to Ellinwood disclose self-powered medication systems that have programmable miniaturized dispensing means. U.S. Pat. No. 4,360,019 to Jassawalla discloses an implantable infusion device that includes an actuating means for delivery of the drug through a catheter. The actuating means includes a solenoid driven miniature pump. All of these devices include miniature power-driven mechanical parts that are required to operate in the body, i.e., they must retract, dispense, or pump. These are complicated and subject to breakdown. Moreover, due to complexity and size restrictions, they are unsuitable to deliver more than a few drugs or drug mixtures at a time.

It therefore would be desirable to provide a multi-welled delivery device that is relatively simple to use and manufacture, but which is dependable and capable of delivering drugs or other molecules and can operate for weeks or years at a time. It would also be desirable to provide such a device that provides the delivery of drugs or other molecules in a controlled manner, such as continuously or pulsatile, and which operates actively or passively. It would further be desirable to provide such a device that can hold many different drugs or other molecules of varying dosages and is small enough to be implanted.

SUMMARY OF THE INVENTION

Devices are provided for the controlled release of molecules. The devices include (1) a substrate comprised of two or more substrate portions bonded together, (2) at least two reservoirs in the substrate containing the molecules for release, and (3) a reservoir cap positioned on, or within a portion of, the reservoir and over the molecules, so that the molecules are controllably released from the device by diffusion through or upon disintegration of the reservoir caps. In a preferred embodiment, the substrate comprises an upper substrate portion adjacent the reservoir cap and a lower substrate portion distal the reservoir cap, such that a reservoir section in the upper substrate portion is in communication with a reservoir section in the lower substrate portion, the two reservoir sections forming a single reservoir which generally is larger than that which would be provided using the single substrate device.

In an alternative embodiment, an internal reservoir cap is interposed between a reservoir section of the upper substrate portion and a reservoir section of the lower substrate portion, wherein release of the molecules from the reservoir section in the lower substrate portion is controlled by diffusion through or disintegration of the internal reservoir cap. The internal reservoir cap can be disintegratable so that the two reservoir sections thereby form a single reservoir. In this alternative embodiment, the reservoir section of the lower substrate portion can contain molecules different in quantity, type, or both quantity and type, from the molecules contained in the reservoir section of the upper substrate portion.

In a preferred embodiment, the molecule to be delivered is a drug. The drug can be provided alone or in a release system, such as a biodegradable matrix, or in any other pharmaceutically acceptable carrier. Combinations of different drugs can be delivered in different reservoirs or even in different reservoir sections as in the embodiment containing internal reservoir caps. The reservoirs can contain multiple drugs or other molecules in variable dosages.

Methods for making these microchip devices are also provided. In preferred embodiments, reservoirs are etched into two or more substrate portions using either chemical (wet) etching or plasma (dry) etching techniques well known in the field of microfabrication. Hundreds to thousands of reservoirs can be fabricated on a single substrate portion using these techniques. SOI techniques also can be adapted to make the reservoirs. The reservoir sections of the substrate portions are aligned and then the portions are bonded together. The reservoirs, or portions thereof, are filled either prior to or after the portions are bonded together.

Each of the reservoirs of a single microchip can contain different molecules and/or different amounts and concentrations, which can be released independently. The filled reservoirs can be capped with materials that passively disintegrate, materials that allow the molecules to diffuse passively out of the reservoir over time, or materials that disintegrate upon application of an electric potential. Release from an active device can be controlled by a preprogrammed microprocessor, remote control, or by biosensors.

BRIEF DESCRIPTION OF THE DRAWINGS

FIGS. 8a-c are schematic views of several configurations of active delivery devices.

FIGS. 9a-e are cross-sectional schematic views of various embodiments of devices having substrates formed from two fabricated substrate portions which have been joined together.

DETAILED DESCRIPTION OF THE INVENTION

Figure 1:
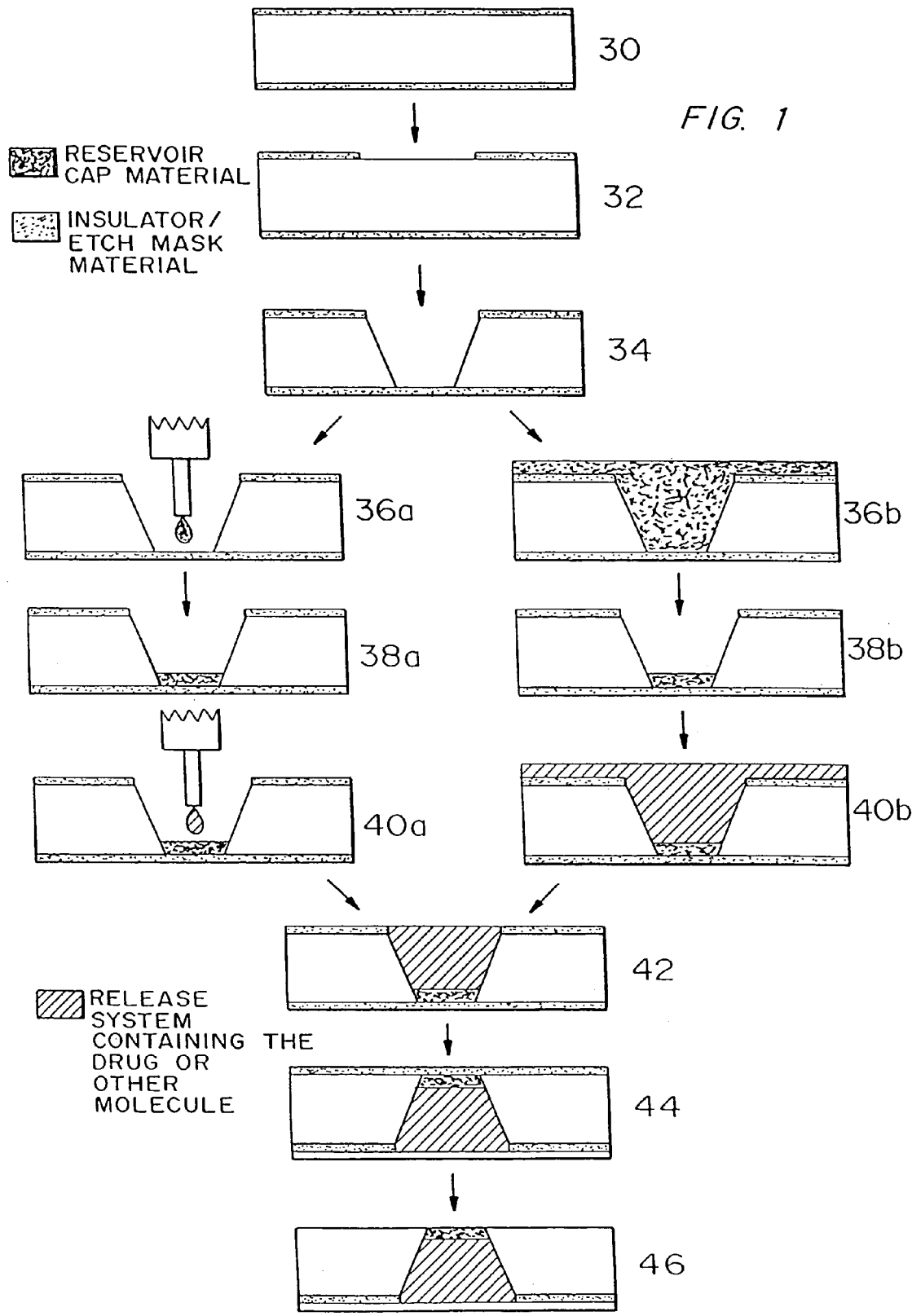
FIG. 1 depicts a typical fabrication scheme for a passive delivery device.

Microchip devices have been provided which can accurately deliver drugs and other molecules at defined rates and times according to the needs of the patient or other experimental system. As used herein, a "microchip" is a miniaturized device fabricated using methods commonly applied to the manufacture of integrated circuits and MEMS (MicroElectroMechanical Systems) such as ultraviolet (UV) photolithography, reactive ion etching, and electron beam evaporation, as described, for example, by Wolf & Tauber, *Silicon Processing for the VLSI Era, Volume 1—Process Technology* (Lattice Press, Sunset Beach, Calif., 1986); and Jaeger, *Introduction to Microelectronic Fabrication*, Volume V in *The Modular Series on Solid State Devices* (Addison-Wesley, Reading, Mass., 1988), as well as MEMS methods that are not standard in making computer chips, including those described, for example, in Madou, *Fundamentals of Microfabrication* (CRC Press, 1997) and micromolding and micromachining techniques known in the art. The microchips provide control over the rate the molecules are released as well as the time at which release begins. The time of release can be controlled passively or actively. The microchip fabrication procedure allows the manufacture of devices with primary dimensions (length of a side if square or rectangular, or diameter if circular) ranging from less than a millimeter to several centimeters. A typical device thickness is 300 μm. However, the thickness of the device can vary from approximately 10 μm to several millimeters, depending on the device's application. Total device thickness and reservoir volume can also be increased by bonding or attaching additional silicon wafers or other substrate materials to the fabricated microchip device. In general, changing the device thickness affects the maximum number of reservoirs that may be incorporated onto a microchip and the volume of each reservoir. In vivo applications of the device would typically require devices having a primary dimension of 2 cm or smaller. Devices for in vivo applications are small enough to be swallowed or implanted using minimally invasive procedures. Smaller in vivo devices (on the order of a millimeter) can be implanted using a catheter or other injectable means. Devices for in vitro applications have fewer size restrictions and, if necessary, can be made much larger than the dimension ranges for in vivo devices.

I. Device Components and Materials

Each device consists of a substrate, reservoirs, and a release system containing, enclosing, or layered with the molecules to be delivered. Devices which control the release time of the molecules may include reservoir caps. Active devices may include control circuitry and a power source.

A. The Substrate

The substrate contains the etched, molded, or machined reservoirs and serves as the support for the microchip. Any material which can serve as a support, is suitable for etching, molding, or machining, and is impermeable to the molecules to be delivered and to the surrounding fluids, for example, water, blood, electrolytes or other solutions, may be used as a substrate. Examples of substrate materials include ceramics, semiconductors, and degradable and non-degradable polymers. Biocompatibility of the substrate material is preferred, but not required. For in vivo applications, non-biocompatible materials may be encapsulated in a biocompatible material, such as poly(ethylene glycol) or polytetrafluoroethylene-like materials, before use. One example of a strong, non-degradable, easily etched substrate that is impermeable to the molecules to be delivered and the surrounding fluids is silicon. In another embodiment, the substrate is made of a strong material that degrades or dissolves over a period of time into biocompatible components. This embodiment is preferred for in vivo applications where the device is implanted and physical removal of the device at a later time is not feasible or recommended, for example, brain implants. An example of a class of strong, biocompatible materials are the poly(anhydride-co-imides) discussed by K. E. Uhrich et al., "Synthesis and characterization of degradable poly(anhydride-co-imides)", *Macromolecules,* 28: 2184-93 (1995).

The substrate can be formed of only one material or can be a composite or multi-laminate material, e.g., several layers of the same or different substrate materials that are bonded together. Multi-portion substrates can include any number of layers of silicon, glasses, ceramics, semiconductors, metals, polymers, or other substrate materials. Two or more complete microchip devices also can be bonded together to form multi-portion substrate devices (see, e.g., FIGS. 9a-e).

B. Release System

The molecules to be delivered may be inserted into the reservoirs in their pure form, as a liquid solution or gel, or they may be encapsulated within or by a release system. As used herein, "release system" includes both the situation where the molecules are in pure form, as either a solid or liquid, or are in a matrix formed of degradable material or a material which releases incorporated molecules by diffusion out of or disintegration of the matrix. The molecules can be sometimes contained in a release system because the degradation, dissolution or diffusion properties of the release system provide a method for controlling the release rate of the molecules. The molecules can be homogeneously or heterogeneously distributed within the release system. Selection of the release system is dependent on the desired rate of release of the molecules. Both non-degradable and degradable release systems can be used for delivery of molecules. Suitable release systems include polymers and polymeric matrices, non-polymeric matrices, or inorganic and organic excipients and diluents such as, but not limited to, calcium carbonate and sugar. Release systems may be natural or synthetic, although synthetic release systems are preferred due to the better characterization of release profiles. The release system is selected based on the period over which release is desired, generally in the range of at least three to twelve months for in vivo applications. In contrast, release times as short as a few seconds may be desirable for some in vitro applications. In some cases, continuous (constant) release from a reservoir may be most useful. In other cases, a pulse (bulk) release from a reservoir may provide more effective results. Note that a single pulse from one reservoir can be transformed into pulsatile release by using multiple reservoirs. It is also possible to incorporate several layers of a release system and other materials into a single reservoir to achieve pulsatile delivery from a single reservoir. Continuous release can be achieved by incorporating a release system that degrades, dissolves, or allows diffusion of molecules through it over an extended period of time. In addition, continuous release can be simulated by releasing several pulses of molecules in quick succession.

The release system material can be selected so that molecules of various molecular weights are released from a reservoir by diffusion out or through the material or degradation of the material. Biodegradable polymers, bioerodible hydrogels, and protein delivery systems are preferred for release of molecules by diffusion, degradation, or dissolution. In general, these materials degrade or dissolve either by enzymatic hydrolysis or exposure to water in vivo or in vitro, or by surface or bulk erosion. Representative synthetic, biodegradable polymers include: poly(amides) such as poly(amino acids) and poly(peptides); poly(esters) such as poly(lactic acid), poly(glycolic acid), poly(lactic-co-glycolic acid), and poly(caprolactone); poly(anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include: poly(ethers) such as poly(ethylene oxide), poly(ethylene glycol), and poly(tetramethylene oxide); vinyl polymers—poly(acrylates) and poly(methacrylates) such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; poly(siloxanes); and any chemical derivatives thereof (substitutions, additions of chemical groups, for example, alkyl, alkylene, hydroxylations, oxidations, and other modifications routinely made by those skilled in the art), copolymers and mixtures thereof.

C. Molecules to be Released

Any natural or synthetic, organic or inorganic molecule or mixture thereof can be delivered. In one embodiment, the microchip is used to deliver drugs systemically to a patient in need thereof. In another embodiment, the construction and placement of the microchip in a patient enables the localized release of drugs that may be too potent for systemic delivery. As used herein, drugs are organic or inorganic molecules, including proteins, nucleic acids, polysaccharides and synthetic organic molecules, having a bioactive effect, for example, anaesthetics, vaccines, chemotherapeutic agents, hormones, metabolites, sugars, immunomodulators, antioxidants, ion channel regulators, and antibiotics. The drugs can be in the form of a single drug or drug mixtures and can include pharmaceutically acceptable carriers. In another embodiment, molecules are released in vitro in any system where the controlled release of a small (milligram to nanogram) amount of one or more molecules is required, for example, in the fields of analytic chemistry or medical diagnostics. Molecules can be effective as pH buffering agents, diagnostic agents, and reagents in complex reactions such as the polymerase chain reaction or other nucleic acid amplification procedures.

D. Reservoir Caps

In the passive timed release drug delivery devices, the reservoir caps are formed from a material that degrades or dissolves over time, or does not degrade or dissolve but is permeable to the molecules to be delivered. These materials are preferably polymeric materials. Materials can be selected for use as reservoir caps to give a variety of degradation rates or dissolution rates or permeabilities to enable the release of molecules from different reservoirs at different times and, in some cases, different rates. To obtain different release times (amounts of release time delay), caps can be formed of different polymers, the same polymer with different degrees of crosslinking, or a UV polymerizable polymer. In the latter case, varying the exposure of this polymer to UV light results in varying degrees of crosslinking and gives the cap material different diffusion properties or degradation or dissolution rates. Another way to obtain different release times is by using one polymer, but varying the thickness of that polymer. Thicker films of some polymers result in delayed release time. Any combination of polymer, degree of crosslinking, or polymer thickness can be modified to obtain a specific release time or rate. In one embodiment, the release system containing the molecules to be delivered is covered by a degradable cap material which is nearly impermeable to the molecules. The time of release of the molecules from the reservoir will be limited by the time necessary for the cap material to degrade or dissolve. In another embodiment, the cap material is non-degradable and is permeable to the molecules to be delivered. The physical properties of the material used, its degree of crosslinking, and its thickness will determine the time necessary for the molecules to diffuse through the cap material. If diffusion out of the release system is limiting, the cap material delays the onset of release. If diffusion through the cap material is limiting, the cap material determines the release rate of the molecules in addition to delaying the onset of release.

In the active timed release devices, the reservoir caps consist of a thin film of conductive material that is deposited over the reservoir, patterned to a desired geometry, and serves as an anode. Cathodes are also fabricated on the device with their size and placement dependent on the device's application and method of electric potential control. The anode is defined as the electrode where oxidation occurs. Any conductive material capable of dissolving into solution or forming soluble ions or oxidation compounds upon application of an electric potential can be used for the fabrication of the anodes and cathodes. In addition, materials that normally form insoluble ions or oxidation products in response to an electric potential can be used if, for example, local pH changes near the anode cause these oxidation products to become soluble. Examples of suitable reservoir cap materials include metals such as copper, gold, silver, and zinc, and some polymers, as described, for example, by I. C. Kwon et al., "Electrically erodible polymer gel for controlled release of drugs", *Nature*, 354: 291-93 (1991); and Y. H. Bae et al., "Pulsatile drug release by electric stimulus", *ACS Symposium Series*, 545: 98-110 (1994).

E. Device Packaging, Control Circuitry, and Power Source

Microelectronic device packages are typically made of an insulating or dielectric material such as aluminum oxide or silicon nitride. Their purpose is to allow all components of the device to be placed in close proximity and to facilitate the interconnection of components to power sources and to each other. For in vivo applications of the delivery device, the entire package, including all components (i.e. the device, the microprocessor, and the power source), are coated or encapsulated in a biocompatible material such as poly(ethylene glycol) or polytetrafluoroethylene-like materials. The materials requirements for in vitro applications may be less stringent and depend on the particular situation.

The control circuitry consists of a timer, a demultiplexer, a microprocessor, and an input source, for example, a memory source, a signal receiver, or a biosensor. The timer and demultiplexer circuitry can be designed and incorporated directly onto the surface of the microchip during electrode fabrication. The criteria for selection of a microprocessor are small size, low power requirement, and the ability to translate the output from memory sources, signal receivers, or biosensors into an address for the direction of power through the demultiplexer to a specific reservoir on the delivery device. Selection of a source of input to the microprocessor such as memory sources, signal receivers, or biosensors depends on the delivery device's particular application and whether device operation is preprogrammed, controlled by remote means, or controlled by feedback from its environment (i.e. biofeedback).

The criteria for selection of a power source are small size, sufficient power capacity, ability to be integrated into the control circuitry, the ability to be recharged, and the length of time before recharging is necessary. Several lithium-based, rechargeable microbatteries have been described by S. D. Jones and J. R. Akridge, "Development and performance of a rechargeable thin-film solid-state microbattery", *Journal of Power Sources,* 54: 63-67 (1995); and J. B. Bates et al., "New amorphous thin-film lithium electrolyte and rechargeable microbattery", *IEEE 35th International Power Sources Symposium,* 337-39 (1992). These batteries are typically only ten microns thick and occupy 1 $cm^2$ of area. One or more of these batteries can be incorporated directly onto the delivery device.

II. Methods of Making the Microchip Devices

A. Fabrication of the Reservoirs

Devices are manufactured using methods known to those skilled in the art, reviewed, for example, by Wolf et al. (1986), Jaeger (1988), and Madou, *Fundamentals of Microfabrication* (CRC Press, 1997).

Figure 2:
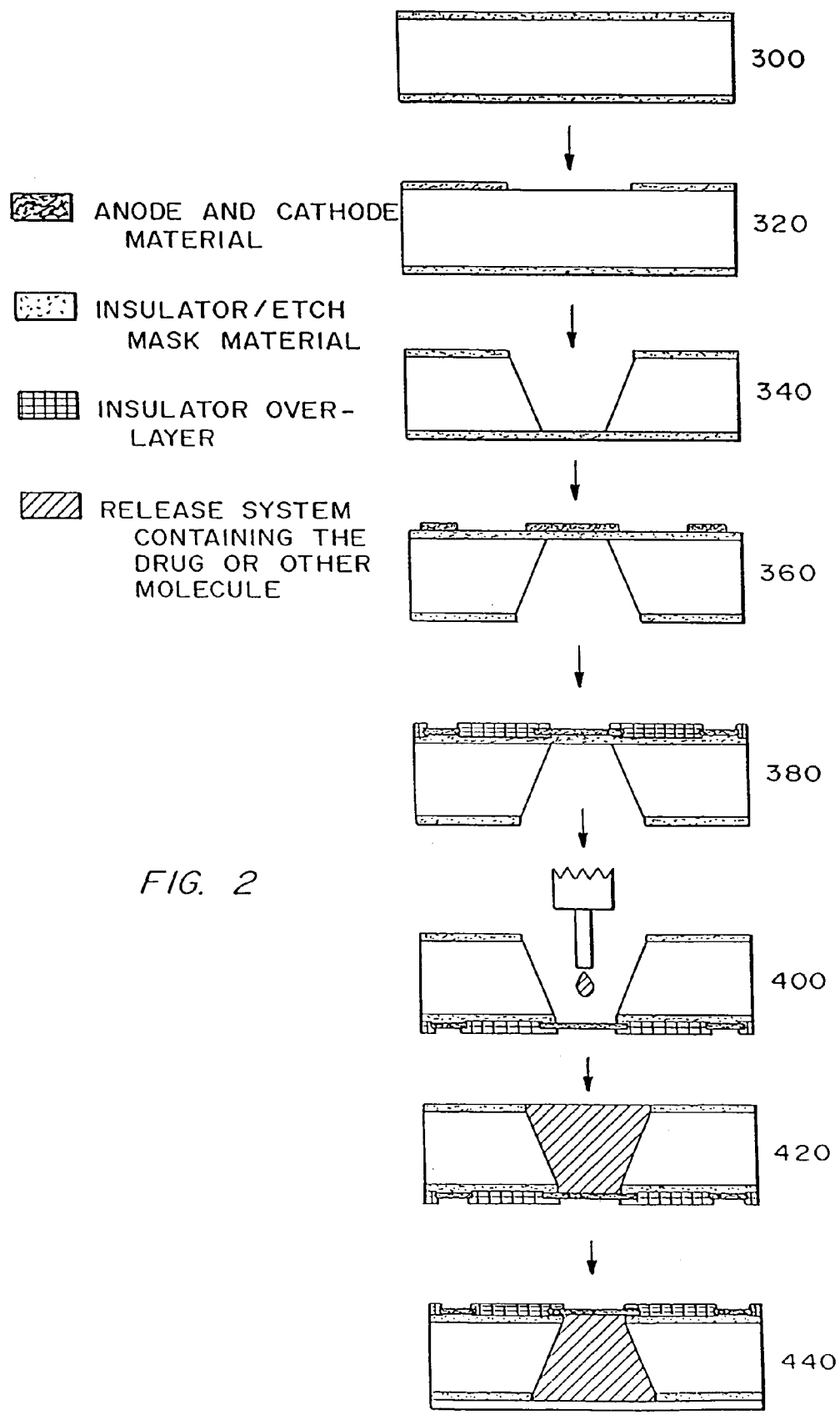
FIG. 2 depicts a typical fabrication scheme for an active delivery device.

In a preferred method of microchip manufacture, depicted in FIGS. 1 and 2, passive and active devices, respectively, fabrication begins by depositing and photolithographically patterning a material, typically an insulating or dielectric material, onto the substrate to serve as an etch mask during reservoir etching. Typical insulating materials for use as a mask include silicon nitride, silicon dioxide, and some polymers, such as polyimide. In a preferred embodiment, a thin film (approximately 1000-3000 Å) of low stress, silicon-rich nitride is deposited on both sides of a silicon wafer 30/300 in a Vertical Tube Reactor (VTR). Alternatively, a stoichiometric, polycrystalline silicon nitride ($Si_3N_4$) can be deposited by Low Pressure Chemical Vapor Deposition (LPCVD), or amorphous silicon nitride can be deposited by Plasma Enhanced Chemical Vapor Deposition (PECVD). Reservoirs are patterned into the silicon nitride film on one side of the wafer 32/320 by ultraviolet photolithography and either plasma etching or a chemical etch consisting of hot phosphoric acid or buffered hydrofluoric acid. The patterned silicon nitride serves as an etch mask for the chemical etching of the exposed silicon 34/340 by a concentrated potassium hydroxide solution (approximately 20-40% KOH by weight at a temperature of 75-90° C.). Alternatively, the reservoirs can be etched into the substrate by dry etching techniques such as reactive ion etching or ion beam etching. These techniques are commonly used in the fabrication of microelectronic devices, as reviewed, for example, by Wolf et al. (1986) and Jaeger (1988). Use of these microfabrication techniques allows the incorporation of hundreds to thousands of reservoirs on a single microchip. The spacing between each reservoir depends on its particular application and whether the device is a passive or active device. In a passive device, the reservoirs may be less than one micron apart. In an active device, the distance between the reservoirs may be slightly larger (between approximately 1 and 10 µm) due to the space occupied by the electrodes on or near each reservoir. Reservoirs can be made in nearly any shape and depth, and need not pass completely through the substrate. In a preferred embodiment, the reservoirs are etched into a (100) oriented, silicon substrate by potassium hydroxide, in the shape of a square pyramid having side walls sloped at 54°, and pass completely through the substrate (approximately 300 µm) to the silicon nitride film on the other side of the substrate, forming a silicon nitride membrane. (Here, the silicon nitride film serves as a potassium hydroxide etch stop.) The pyramidal shape allows easy filling of the reservoirs through the large opening of the reservoir (approximately 500 µm by 500 µm) on the patterned side of the substrate, release through the small opening of the reservoir (approximately 50 µm by 50 µm) on the other side of the substrate, and provides a large cavity inside the device for storing the drugs or other molecules to be delivered.

Multi-portion substrate devices can be formed simply by making two or more individual substrate portions and then bonding them to one another with the matching openings of the reservoir sections aligned. There are two main types of bonds that can be formed between substrate portions. The first are atomic-scale or molecular-scale bonds. These types of bonds usually involve the interpenetration, intermixing, or interdiffusion of atoms or molecules of one or more of the substrates at the interface between the substrate materials. A preferred method of this type of substrate bonding for use primarily with silicon or glass substrates involves using heat and/or electric voltages to enable the interdiffusion of material between the two substrates, causing a molecular-scale bond to form at the interface between silicon, glass, and other similar materials. This anodic bonding process is well known in the art. Another embodiment of this type of bonding involves melting and re-solidification of the top layer of one or both substrates at an interface between two or more substrate portions. The melted material intermixes, and upon solidification, a strong bond is formed between the substrate portions. In one embodiment, this melting and re-solidification can be caused by the brief application of a solvent (for example, methylene chloride) to the substrate, e.g., PLEXIGLAS™ (an acrylic) or LEXAN™ (polycarbonate). The second type of bonding methods involves using a material other than the substrate material to form the bond. A preferred embodiment of this type of bonding includes the use of chemical adhesives, epoxies, and cements. An embodiment that could be used with UV transparent substrate materials would involve UV curable epoxy. The UV curable epoxy would be spread between the two substrate portions using a method such as spin coating, the reservoirs would be aligned, and a UV light source would be used to cross-link (i.e. cure) the epoxy and bond the substrates together.

Alternatively, reservoirs also can be formed using silicon-on-insulator (SOI) techniques, such as is described in S. Renard, "Industrial MEMS on SOI," *J. Micromech. Microeng.* 10: 245-249 (2000). SOI methods can be usefully adapted to form reservoirs having complex reservoir shapes, for example, as shown in FIGS. 9*b*, 9*c*, and 9*e*. SOI wafers behave essentially as two substrate portions that have been bonded on an atomic or molecular-scale before any reservoirs have been etched into either portion. SOI substrates easily allow the reservoirs (or reservoir sections) on either side of the insulator layer to be etched independently, enabling the reservoirs on either side of the insulator layer to have different shapes. The reservoir (portions) on either side of the insulator layer then can be connected to form a single reservoir having a complex geometry by removing the insulator layer between the two reservoirs using methods such as reactive ion etching, laser, ultrasound, or wet chemical etching.

B. Fabrication of Passive Timed Release Reservoir Caps

In FIG. 1, the steps represented by 36a, 38a, and 40a, are conducted using ink jet or microinjection, while represented by 36b, 38b, and 40b, are conducted using spin coating. In the fabrication of passive timed release microchips, the reservoir cap material is injected with a micro-syringe 36a, printed with an inkjet printer cartridge, or spin coated 36b into a reservoir having the thin membrane of insulating mask material still present over the small opening of the reservoir. If injection or inkjet printing methods are used, cap formation is complete after the material is injected or printed into the reservoir 38a and does not require further processing. If spin coating is used, the cap material is planarized by multiple spin coatings 36b. The surface of the film is then etched by a plasma, an ion beam, or chemical etchant until the desired cap thickness is obtained 38b. In a preferred embodiment, the insulating material used is silicon nitride and the cap material is printed into the reservoir with an inkjet cartridge filled with a solution or suspension of the cap material.

Reservoir caps control the time at which molecules are released from the reservoirs. Each reservoir cap can be of a different thickness or have different physical properties to vary the time at which each release system containing the molecules is exposed to the surrounding fluids. Injection, inkjet printing, and spin coating are the preferred methods of reservoir filling and any of these methods may be used to fill reservoirs, regardless of the reservoir's shape or size. However, injection and inkjet printing are the preferred methods of filling deep (>10 μm) reservoirs or reservoirs with large openings (>100 μm). For example, to obtain different cap thicknesses using injection or inkjet printing, different amounts of cap material are injected or printed directly into each individual reservoir. Spin coating is the preferred method of filling shallow (<10 μm) reservoirs, reservoirs that do not pass completely through the substrate, or reservoirs with small (<100 μm) openings. Variation in cap thickness or material by spin coating can be achieved by a repeated, step-wise process of spin coating, masking selected reservoirs, and etching. For example, to vary cap thickness with spin coating, the cap material is spin coated over the entire substrate. Spin coating is repeated, if necessary, until the material is nearly planarized. A mask material such as photoresist is patterned to cover the cap material in all the reservoirs except one. Plasma, ion beam, or chemical etchants are used to etch the cap material in the exposed reservoir to the desired thickness. The photoresist is then removed from the substrate. The process is repeated as a new layer of photoresist is deposited and patterned to cover the cap material in all the reservoirs except one (the exposed reservoir is not the same one already etched to its desired thickness). Etching of the exposed cap material in this reservoir continues until the desired cap thickness is obtained. This process of depositing and patterning a mask material such as photoresist, etching, and mask removal can be repeated until each reservoir has its own unique cap thickness. The techniques, UV photolithography, plasma or ion beam etching, etc., are well known to those skilled in the field of microfabrication.

Although injection, inkjet printing and spin coating are the preferred methods of cap fabrication, it is understood that each reservoir can be capped individually by capillary action, by pulling or pushing the material into the reservoir using a vacuum or other pressure gradient, by melting the material into the reservoir, by centrifugation and related processes, by manually packing solids into the reservoir, or by any combination of these or similar reservoir filling techniques.

Once a cap fabrication method is selected, additional methods for controlling the time of release of molecules from a reservoir can be utilized, for example, including either UV polymerizable polymers or the layering of release system and cap materials. In the first embodiment, where the reservoir caps are made of either an injected, inkjet printed or spin coated UV polymerizable polymer, each cap can be exposed to a different intensity of UV light to give varying degrees of crosslinking and therefore, different degradation or dissolution rates for degradable caps or different permeabilities to the molecules for non-degradable caps. Second, layers of cap material, both degradable and non-degradable, can be inserted between layers of the release system containing the molecules to be delivered by injection, inkjet printing, spin coating, or selective crosslinking. These and other similar methods allow complex release profiles (e.g., pulsatile delivery at irregular time intervals) to be achieved from a single reservoir.

If desired, a passive timed release device can be fabricated without reservoir caps. The rate of release of the molecules is thus solely controlled by the physical and material properties of the release system containing the molecule to be delivered.

Several possible configurations for passive delivery devices are shown in FIG. 7.

C. Fabrication of Active Timed Release Reservoir Caps

In a preferred embodiment, photoresist is patterned in the form of electrodes on the surface of the substrate having the reservoirs covered by the thin membrane of insulating or dielectric material. The photoresist is developed such that the area directly over the covered opening of the reservoir is left uncovered by photoresist and is in the shape of an anode. A thin film of conductive material capable of dissolving into solution or forming soluble ions or oxidation compounds upon the application of an electric potential is deposited over the entire surface using deposition techniques such as chemical vapor deposition, electron or ion beam evaporation, sputtering, spin coating, and other techniques known in the art. Exemplary materials include metals such as copper, gold, silver, and zinc and some polymers, as disclosed by Kwon et al. (1991) and Bae et al. (1994). After film deposition, the photoresist is stripped from the substrate. This removes the deposited film, except in those areas not covered by photoresist (lift-off technique). This leaves conducting material on the surface of the substrate in the form of electrodes 360. An alternative method involves depositing the conductive material over the entire surface of the device, patterning photoresist on top of the conductive film using UV or infrared (IR) photolithography, so that the photoresist lies over the reservoirs in the shape of anodes, and etching the unmasked conductive material using plasma, ion beam, or chemical etching techniques. The photoresist is then stripped, leaving conductive film anodes covering the reservoirs. Typical film thicknesses of the conductive material may range from 0.05 to several microns. The anode serves as the reservoir cap and the placement of the cathodes on the device is dependent upon the device's application and method of electric potential control.

An insulating or dielectric material such as silicon oxide ($SiO_x$) or silicon nitride ($SiN_x$) is deposited over the entire surface of the device by methods such as chemical vapor deposition (CVD), electron or ion beam evaporation, sputtering, or spin coating. Photoresist is patterned on top of the dielectric to protect it from etching except on the cathodes and the portions of the anodes directly over each reservoir 380. The dielectric material can be etched by plasma, ion beam, or chemical etching techniques. The purpose of this film is to protect the electrodes from corrosion, degradation, or dissolution in all areas where electrode film removal is not necessary for release.

The electrodes are positioned in such a way that when an electric potential is applied between an anode and a cathode, the unprotected (not covered by dielectric) portion of the anode reservoir cap oxidizes to form soluble compounds or ions that dissolves into solution, exposing the release system containing the molecules to the surrounding fluids. The molecules are released from the reservoir at a rate dependent upon the degradation or dissolution rate of a degradable release system or the rate of diffusion of the molecules out of or through a non-degradable release system.

Several possible configurations for active delivery devices are shown in FIG. 8.

D. Removal of the Insulator Membrane (Reservoir Etch Stop)

The thin membrane of insulating or dielectric material covering the reservoir used as a mask and an etch stop during reservoir fabrication must be removed from the active timed release device before filling reservoir 400 and from the passive timed release device (if the reservoir extends completely through the substrate) after filling reservoir 44. The membrane may be removed in two ways. First, the membrane can be removed by an ion beam or reactive ion plasma. In a preferred embodiment, the silicon nitride used as the insulating material can be removed by a reactive ion plasma composed of oxygen and fluorine containing gases such as $CHF_3$, $CF_4$, or $SF_6$. Second, the membrane can be removed by chemical etching. For example, buffered hydrofluoric acid (BHF or BOE) can be used to etch silicon dioxide and hot phosphoric acid can be used to etch silicon nitride.

E. Reservoir Filling

The release system containing the molecules for delivery is inserted into the large opening of the reservoir by injection, inkjet printing or spin coating 40a/40b/400. Each reservoir can contain a different molecule and dosage. Similarly, the release kinetics of the molecule in each reservoir can be varied by the choice of the release system and cap materials. In addition, the mixing or layering of release system and cap materials in each reservoir can be used to tailor the release kinetics to the needs of a particular application.

The distribution over the microchip of reservoirs filled with the release system containing the molecules to be delivered can vary depending on the medical needs of the patient or other requirements of the system. For applications in drug delivery, for example, the drugs in each of the rows can differ from each other. One row may contain a hormone and another row may contain a metabolite. Also, the release system can differ within each row to release a drug at a high rate from one reservoir and a slow rate from another reservoir. The dosages can also vary within each row. For those devices having deep (>10 μm) reservoirs or reservoirs with large (>100 μm) openings, differences in reservoir loading can be achieved by injection or inkjet printing of different amounts of material directly into each reservoir. Variation between reservoirs is achieved in devices having shallow (<10 μm) reservoirs, reservoirs that do not pass completely through the substrate, or reservoirs with small (<100 μm) openings by a repeated, step-wise process of masking selected reservoirs, spin coating, and etching, as described above regarding the fabrication by spin coating of passive timed release reservoir caps. Preferably, the release system and molecules to be delivered are mixed before application to the reservoirs. Although injection, inkjet printing and spin coating are the preferred methods of filling reservoirs, it is understood that each reservoir can be filled individually by capillary action, by pulling or pushing the material into the reservoir using a vacuum or other pressure gradient, by melting the material into the reservoir, by centrifugation and related processes, by manually packing solids into the reservoir, or by any combination of these or similar reservoir filling techniques.

In preferred embodiments of both active and passive release devices, the reservoir openings used for filling (i.e., the openings opposite the reservoir cap end) are sealed following reservoir filling, using any of a variety of techniques known in the art. For example, sealing can be provided by bonding a rigid backing plate or a thin flexible film across the opening. Alternatively, the opening can be sealed by applying a fluid material, e.g., an adhesive, which plugs the opening and hardens to form a seal. In another embodiment, a second substrate portion, e.g., of a second device, can be bonded across the reservoirs openings, as shown in FIG. 9.

F. Device Packaging, Control Circuitry, and Power Source

The openings through which the reservoirs of passive and active devices are filled are sealed by wafer bonding or with a waterproof epoxy or other appropriate material impervious to the surrounding fluids 44/440. For in vitro applications, the entire unit, except for the face of the device containing the reservoirs and electrodes, is encased in a material appropriate for the system. For in vivo applications, the unit is preferably encapsulated in a biocompatible material such as poly(ethylene glycol) or polytetrafluoroethylene.

Figure 3:
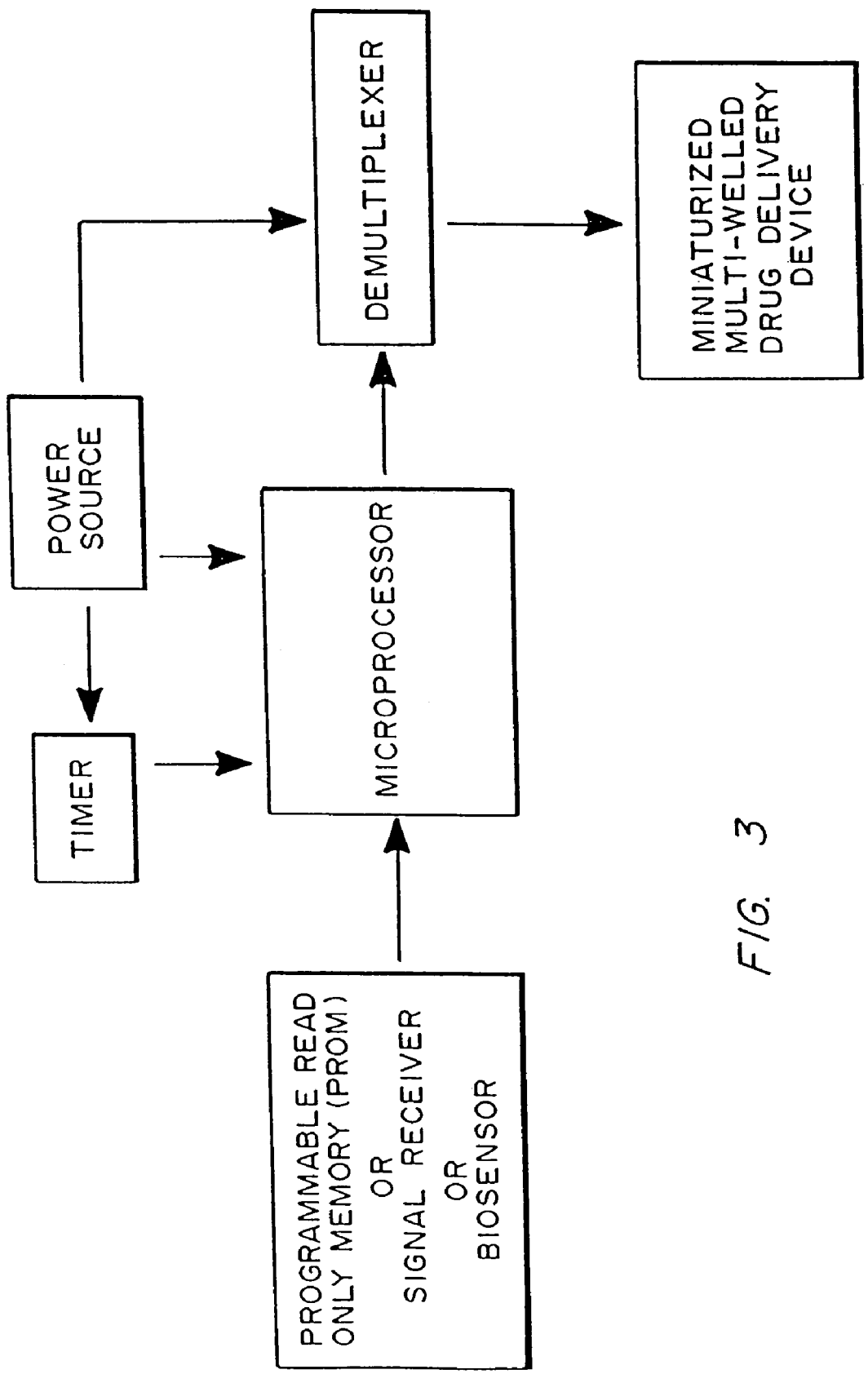
FIG. 3 depicts a typical device control circuitry flowsheet.

The mechanism for release of molecules by the active timed release device does not depend on multiple parts fitted or glued together which must retract or dislodge. Control of the time of release of each reservoir can be achieved by a preprogrammed microprocessor, by remote control, by a signal from a biosensor, or by any combination of these methods, as shown schematically in FIG. 3. First, a microprocessor is used in conjunction with a source of memory such as programmable read only memory (PROM), a timer, a demultiplexer, and a power source such as a microbattery, such as is described, for example, by Jones et al. (1995) and Bates et al. (1992). The release pattern is written directly into the PROM by the user. The PROM sends these instructions to the microprocessor. When the time for release has been reached as indicated by the timer, the microprocessor sends a signal corresponding to the address (location) of a particular reservoir to the demultiplexer. The demultiplexer sends an input, such as an electric potential, to the reservoir addressed by the microprocessor. A microbattery provides the power to operate the PROM, timer, and microprocessor, and provides the electric potential input that is directed to a particular reservoir by the demultiplexer. The manufacture, size, and location of each of these components is dependent upon the requirements of a particular application. In a preferred embodiment, the memory, timer, microprocessor, and demultiplexer circuitry is integrated directly onto the surface of the chip. The microbattery is attached to the other side of the chip and is connected to the device circuitry by vias or thin wires. However, in some cases, it is possible to use separate, prefabricated, component chips for memory, timing, processing, and demultiplexing. These are attached to the backside of the miniaturized delivery device with the battery. The size and type of prefabricated chips used depends on the overall dimensions of the delivery device and the number of reservoirs. Second, activation of a particular reservoir by the application of an electric potential can be controlled externally by remote control. Much of the circuitry used for remote control is the same as that used in the preprogrammed method. The main difference is that the PROM is replaced by a signal receiver. A signal such as radio waves, microwaves, low power laser, or ultrasound is sent to the receiver by an external source, for example, computers or ultrasound generators. The signal is sent to the microprocessor where it is translated into a reservoir address. Power is then directed through the demultiplexer to the reservoir having the appropriate address. Third, a biosensor is integrated into the microchip to detect molecules in the surrounding fluids. When the concentration of the molecules reaches a certain level, the sensor sends a signal to the microprocessor to activate one or more reservoirs. The microprocessor directs power through the demultiplexer to the particular reservoir(s).

G. Electric Potential Control Methods

The reservoir caps of an active device are anodes that oxidize to form soluble compounds and ions when a potential is applied between the anode and a cathode. For a given electrode material and electrolyte, there exists a range of electric potentials over which these oxidation reactions are thermodynamically and kinetically favorable. In order to reproducibly oxidize and open the reservoir caps of the device, the anode potential must be maintained within this favorable potential range.

There exist two primary control methods for maintaining an electrode within a specific potential range. The first method is called potentiostatic control. As the name indicates, the potential is kept constant during reservoir activation. Control of the potential is typically accomplished by incorporating a third electrode into the system that has a known, constant potential, called a reference electrode. The reference electrode can take the form of an external probe whose tip is placed within one to three millimeters of the anode surface. The potential of the anode is measured and controlled with respect to the known potential of a reference electrode such as a saturated calomel electrode (SCE). In a preferred embodiment of potentiostatic control, a thin film reference electrode and potential feedback controller circuitry could be fabricated directly onto the surface of the microchip. For example, a microfabricated Ag/AgCl reference electrode integrated with a microchip device would enable the device to maintain the anode potential of an activated reservoir within the oxidation regime until the reservoir was completely opened. The second method is called galvanostatic control. As the name indicates, the current is kept constant during reservoir activation. One drawback to this method of control is that there is more than one stable potential for a given current density. However, if the current density versus potential behavior is well characterized for the microchip device in a particular electrolyte system, the current density that will maintain the anode in the oxidation regime will be known. In this case, the galvanostatic method of potential control would be preferable to the potentiostatic control, because galvanostatic control does not require a reference electrode.

III. Applications for the Microchip Devices

Passive and active microchip devices have numerous in vitro and in vivo applications. The microchip can be used in vitro to deliver small, controlled amounts of chemical reagents or other molecules to solutions or reaction mixtures at precisely controlled times and rates. Analytical chemistry and medical diagnostics are examples of fields where the microchip delivery device can be used. The microchip can be used in vivo as a drug delivery device. The microchips can be implanted into a patient, either by surgical techniques or by injection, or can be swallowed. The microchips provide delivery of drugs to animals or persons who are unable to remember or be ambulatory enough to take medication. The microchips further provide delivery of many different drugs at varying rates and at varying times of delivery.

In a preferred embodiment, the reservoir cap enables passive timed release, not requiring a power source, of molecules. The reservoirs are capped with materials that degrade or dissolve at a known rate or have a known permeability (diffusion constant) for the molecules to be delivered. Therefore, the degradation, dissolution or diffusion characteristics of the cap material determine the time at which the release of molecules in a particular reservoir begins. In effect, the microchip provides dual control of the release of molecules by selection of the release system (rate controller) and selection of the cap material (time controller, and in some cases, rate controller).

In another preferred embodiment, the reservoir cap enables active timed release, requiring a power source, of molecules. In this embodiment, the reservoir caps consist of a thin film of conductive material that is deposited over the reservoir, patterned to a desired geometry, and serves as an anode. Cathodes are also fabricated on the device with their size and placement dependent on the device's application and method of electric potential control. Conductive materials capable of dissolving into solution or forming soluble compounds or ions upon the application of an electric potential, including metals such as copper, gold, silver, and zinc and some polymers, are used in the active timed release device. When an electric potential is applied between an anode and cathode, the conductive material of the anode above the reservoir oxidizes to form soluble compounds or ions that dissolve into solution, exposing the release system containing the molecules to be delivered to the surrounding fluids. Alternatively, the application of an electric potential can be used to create changes in local pH near the anode reservoir cap to allow normally insoluble ions or oxidation products to become soluble. This would allow the reservoir to dissolve and expose the release system to the surrounding fluids. In either case, the molecules to be delivered are released into the surrounding fluids by diffusion out of or by degradation or dissolution of the release system. The frequency of release is controlled by incorporation of a miniaturized power source and microprocessor onto the microchip. Activation of any reservoir can be achieved by preprogramming the microprocessor, by remote control, or by a signal from a biosensor.

The microchip devices and methods of fabrication thereof will be further understood by reference to the following non-limiting examples.

EXAMPLE 1

Fabrication of Active Release Microchip

1) Obtain double side polished, prime grade, (100) oriented silicon wafers.
   Wafer thickness=approximately 295-310 μm
2) Deposit approximately 1600-1900 Å of low stress (10:1, silicon rich) silicon nitride on both sides of the wafers in an SVG/Thermco 7000 Series vertical tube reactor (VTR).
   Gas Flows: Ammonia ($NH_3$)=24 sccm
   Dichlorosilane ($SiH_2Cl_2$)=253 sccm
   Temperature=780° C.
   Chamber Pressure=268 mtorr
   Deposition Rate=approximately 30 Å/min.
3) Pattern positive photoresist (PR) as squares (approximately 500 μm by 500 μm) serving as the large reservoir openings on one side of the wafers having low stress silicon nitride deposited on them.

Hexamethyldisilazane deposition on both sides of the wafer
("HMDS vapor prime") in vacuum oven
approximately 30 min. at 150° C.
Photoresist (PR) Type—OCG825-20
PR Spin Speed and Times (for a Solitec Inc. Model 5110 spinner)
7 sec. at 500 rpm (coat)
7 sec. at 750 rpm (spread)
30 sec. at 3500 rpm (spin)
Prebake (in Blue M Model DDC-146C oven)
30 min. at 90° C.
Ultraviolet (UV) exposure for each wafer in the contact aligner (Karl Suss Model MA4) with patterned mask
32 sec. at wavelength=320 nm
Developer Type —OCG934 1:1
Put exposed wafers into slightly agitated, room temperature developer
Develop Time=approximately 40 seconds
Cascade Rinse=2 min.
Rinse and Dry Wafers in Spin Rinse Dryer (SRD)
Postbake (in Blue M Model DDC-146C oven)
30 min. at 120° C.
4) Etch the VTR nitride to the underlying silicon using a plasma etcher (Plasmaquest Series II Reactor Model 145).
Gas Flows: Oxygen ($O_2$)=2 sccm
Helium (He)=15 sccm
Carbon Tetrafluoride ($CF_4$)=15 sccm
Power: RF=10 W
ECR=100 W
Chamber Pressure=20 mtorr
Temperature=25° C.
Nitride Etch Rate=approximately 350 Å/min
5) Remove excess PR with solvents—acetone, methanol, isopropanol.
6) Etch the exposed silicon in aqueous potassium hydroxide (KOH) in a wet processing hood (by Semifab, Inc.).
Concentration=approximately 38-40% by weight
Temperature=approximately 85-90° C.
Etch Rate=approximately 1 m/min
7) Post-KOH clean in a wet processing hood (by Laminaire Corp.) to avoid $K^+$ contamination in cleanroom.
Piranha Clean for 15 min.
Dump Rinse=3 times
Hydrofluoric Acid (HF) Dip
10 sec. in 50:1 water:HF solution (by volume)
Dump Rinse=3 times
Standard RCA clean
Rinse and Dry in SRD
8) Pattern image reversal PR over the nitride membranes for subsequent gold liftoff process.
HMDS vapor prime in vacuum oven
approximately 30 min. at 150° C.
Photoresist Type (PR)-AZ 5214 E
PR Spin Speed and Times (for a Solitec Inc. Model 5110 spinner)
6 sec. at 500 rpm (coat)
6 sec. at 750 rpm (spread)
30 sec. at 4000 rpm (spin)
Prebake (in Blue M Model DDC-146C oven): 30 min. at 90° C.
Ultraviolet (UV) exposure for each wafer in the contact aligner (Karl Suss Model MA4) with patterned mask
40 sec. at wavelength=320 nm
Bake for 90 sec. on a metal plate in an oven at 120° C. (Blue M Model DDC-146C)
UV flood exposure for each wafer in the contact aligner (Karl Suss Model MA4) WITHOUT a patterned mask (expose entire wafer)
Approximately 200 sec. at wavelength=320 nm
Developer Type—AZ 422 MIF
Put exposed wafers into slightly agitated, room temperature developer
Develop Time=approximately 1 min. 30 sec.
Cascade Rinse=2 min.
Rinse and Dry Wafers in Spin Rinse Dryer (SRD)
9) Evaporation of gold onto the image reversal PR patterned side of each wafer using a liftoff plate (wafer holder) in an electron beam evaporator (Temescal Semiconductor Products Model VES 2550).
Gold Deposition Rate=5 Å/sec.
Gold Thickness=approximately 3000 Å
Base Pressure=approximately $5.0 \times 10^{-7}$ torr
Room Temperature (no outside heating or cooling)
10) Liftoff gold layer with acetone.
11) Clean wafers with solvents—acetone, methanol, isopropanol.
12) Oxygen plasma clean (ash) in a plasma etcher (Plasmaquest Series II Reactor Model 145).
Gas Flows: $O_2$=25 sccm
He=15 sccm
Power: RF=10 W
ECR=200 W
Chamber Pressure=20 mtorr
Temperature=25° C.
13) Deposit plasma-enhanced chemical vapor deposition (PECVD) silicon dioxide over the entire surface of the wafers having the gold electrodes on them using a PECVD chamber (Plasma-Therm 700 Series Waf'r/Batch Dual Chamber Plasma Processing System).
Gas Flows: 2% $SiH_4$ in $N_{2=400}$ sccm
$N_2O$=900 sccm
RF Power=20 W
Chamber Pressure=900 mtorr
Deposition Rate=approximately 250-500 Å/min.
Temperature=350° C.
14) Clean wafers with solvents—acetone, methanol, isopropanol.
15) Pattern PR to expose portions of the silicon dioxide covering parts of the gold electrodes.
HMDS vapor prime in vacuum oven
approximately 30 min. at 150° C.
Photoresist (PR) Type —OCG825-20
PR Spin Speed and Times (for a Solitec Inc. Model 5110 spinner)
7 sec. at 500 rpm (coat)
7 sec. at 750 rpm (spread)
30 sec. at 3500 rpm (spin)
Prebake (in Blue M Model DDC-146C oven): 30 min. at 90° C.
Ultraviolet (UV) exposure for each wafer in the contact aligner (Karl Suss Model MA4) with patterned mask
32 sec. at wavelength=320 nm
Developer Type—OCG934 1:1
Put exposed wafers into slightly agitated, room temperature developer
Develop Time=approximately 55 seconds
Cascade Rinse=2 min.
Rinse and Dry Wafers in Spin Rinse Dryer (SRD)
Postbake (in Blue M Model DDC-146C oven): 30 min. at 120° C.

16) Etch the exposed silicon dioxide to the gold surface with a plasma etcher (Plasmaquest Series II Reactor Model 145).
   Gas Flows: He=15 sccm
      $CF_{4=15}$ sccm
   Power: RF=10 W
      ECR=100 W
   Chamber Pressure=20 mtorr
   Temperature=15° C.
   Silicon Dioxide Etch Rate=approximately 215 Å/min.
17) Spin photoresist on the side of the wafers having the gold electrodes to protect the electrodes during wafer dicing.
   Photoresist (PR) Type —OCG825-20
   PR Spin Speed and Times (for a Solitec Inc. Model 5110 spinner)
      7 sec. at 500 rpm (coat)
      7 sec. at 750 rpm (spread)
      30 sec. at 3.500 rpm (spin)
   Prebake (in Blue M Model DDC-146C oven): 30 min. at 90° C.
18) Dice the wafers with a diesaw (Disco Automatic Dicing Saw Model DAD-2H/6T).
   Process yields 21 devices per 4" wafer with each device measuring 17 mm by 17 mm on a side
19) Etch the nitride membrane from the back of the devices with a plasma etcher (Plasmaquest Series II Reactor Model 145).
   Gas Flows: $O_2$=2 sccm
      He=15 sccm
      $CF_4$=15 sccm
   Power: RF=10 W
      ECR=100 W
   Chamber Pressure=20 mtorr
   Temperature=25° C.
   Nitride Etch Rate=approximately 350 Å/min.
20) Clean the devices with solvents and $O_2$ plasma.
   Solvent clean—acetone, methanol, isopropanol
   Oxygen plasma clean with a plasma etcher (Plasmaquest Series II Reactor Model 145)
      Gas Flows: $O_2$=25 sccm
         He=15 sccm
      Power: RF=10 W
         ECR=200 W
      Chamber Pressure=20 mtorr
      Temperature=25° C.

Fabrication of active microchip devices is complete.

EXAMPLE 2

Fabrication of Passive Release Microchip

1) Obtain double side polished, prime grade, (100) oriented silicon wafers for devices having reservoirs extending completely through the wafer or single side polished, prime grade, (100) oriented silicon wafers for devices having reservoirs that do not extend completely through the wafer.
   Wafer thickness=approximately 295-310 μm for devices with reservoirs extending completely through the wafer (devices that do not have reservoirs extending all the way through the wafer can be of any desired thickness)
2) Deposit approximately 1600-1900 Å of low stress (10:1, silicon rich) silicon nitride on both sides of the wafers in an SVG/Thermco 7000 Series vertical tube reactor (VTR).
   Gas Flows: Ammonia ($NH_3$)=24 sccm
      Dichlorosilane ($SiH_2Cl_2$)=253 sccm
   Temperature=780° C.
   Chamber Pressure=268 mtorr
   Deposition Rate=approximately 30 Å/min.
3) Pattern positive PR as squares (approximately 500 μm by 500 μm for devices with reservoirs extending completely through the wafer or any desired dimension for devices that do not have reservoirs extending all the way through the wafer) serving as the large reservoir openings on one side of the wafers having low stress silicon nitride deposited on them.
   Hexamethyldisilazane deposition on both sides of the wafer
      ("HMDS vapor prime") in vacuum oven
      approximately 30 min. at 150° C.
   Photoresist (PR) Type—OCG825-20
   PR Spin Speed and Times (for a Solitec Inc. Model 5110 spinner)
      7 sec. at 500 rpm (coat)
      7 sec. at 750 rpm (spread)
      30 sec. at 3500 rpm (spin)
   Prebake (in Blue M Model DDC-146C oven)
      30 min. at 90° C.
   Ultraviolet (UV) exposure for each wafer in the contact aligner (Karl Suss Model MA4) with patterned mask
      32 sec. at wavelength=320 nm
   Developer Type —OCG934 1:1
   Put exposed wafers into slightly agitated, room temperature developer
      Develop Time=approximately 40 seconds
   Cascade Rinse=2 min.
   Rinse and Dry Wafers in Spin Rinse Dryer (SRD)
   Postbake (in Blue M Model DDC-146C oven): 30 min. at 120° C.
4) Etch the VTR nitride to the underlying silicon using a plasma etcher (Plasmaquest Series II Reactor Model 145).
   Gas Flows: Oxygen ($O_2$)=2 sccm
      Helium (He)=15 sccm
      Carbon Tetrafluoride ($CF_4$)=15 sccm
   Power: RF=10 W
      ECR=100 W
   Chamber Pressure=20 mtorr
   Temperature=25° C.
   Nitride Etch Rate=approximately 350 Å/min.
5) Remove excess PR with solvents—acetone, methanol, isopropanol.
6) Etch the exposed silicon in aqueous potassium hydroxide (KOH) in a wet processing hood (by Semifab, Inc.).
   Concentration=approximately 38-40% by weight
   Temperature=approximately 85-90° C.
   Etch Rate=approximately 1 μm/min.
7) Post-KOH clean in a wet processing hood (by Laminaire Corp.) to avoid $K^+$ contamination in cleanroom.
   Piranha Clean for 15 min.
   Dump Rinse=3 times
   Hydrofluoric Acid (HF) Dip
      10 sec. in 50:1 water:HF solution (by volume)
   Dump Rinse=3 times
   Standard RCA clean
   Rinse and Dry in SRD For those devices not having a nitride membrane (reservoirs not extending completely through the wafer), fabrication of passive microchip device is complete. Dice the wafer into individual devices. The reservoirs of each device are ready to be filled.

Alternately, for those devices having a nitride membrane (reservoirs extend completely through the wafer), continue with the following steps.

8) Fill the reservoir using injection, inkjet printing, spin coating or another method with reservoir cap materials, release system, and molecules to be released, or any combination thereof.
9) Seal the reservoir openings on the side of the wafer through which the reservoirs were filled.
10) Etch the nitride membranes on the side of the wafer opposite the filling side by using a plasma etcher (Plasmaquest Series II Reactor Model 145) until the cap material or release system is reached (etch parameters may vary depending on the type of cap material or release system under the nitride).

Gas Flows: Oxygen ($O_2$)=2 sccm
  Helium (He)=15 sccm
  Carbon Tetrafluoride ($CF_4$)=15 sccm
Power: RF=10 W
  ECR=100 W
Chamber Pressure=20 mtorr
Temperature=25° C.
Nitride Etch Rate=approximately 350 Å/min.

11) Spin photoresist on the side of the wafers having exposed cap materials or release system to protect them during wafer dicing (this step may not be necessary, depending on the type of exposed cap material or release system).

Photoresist (PR) Type —OCG825-20
PR Spin Speed and Times (for a Solitec Inc. Model 5110 spinner)
  7 sec. at 500 rpm (coat)
  7 sec. at 750 rpm (spread)
  30 sec. at 3500 rpm (spin)
Prebake (in Blue M Model DDC-146C oven): 30 min. at 90° C.

12) Dice the wafers with a diesaw (Disco Automatic Dicing Saw Model DAD-2H/6T).

Process yields 21 devices per 4" wafer with each device measuring 17 mm by 17 mm on a side 13) Clean the devices with solvents and $O_2$ plasma (these steps may not be necessary, depending on the type of exposed cap material or release system).

Solvent clean—acetone, methanol, isopropanol
Oxygen plasma clean in a plasma etcher (Plasmaquest Series II Reactor Model 145)
  Gas Flows: $O_2$=25 sccm
    He=15 sccm
  Power: RF=10 W
    ECR=200 W
  Chamber Pressure=20 mtorr
  Temperature=25° C.

Fabrication of passive microchip device is complete.

EXAMPLE 3

Microchip with Passive Timed Drug Release

Figure 4:
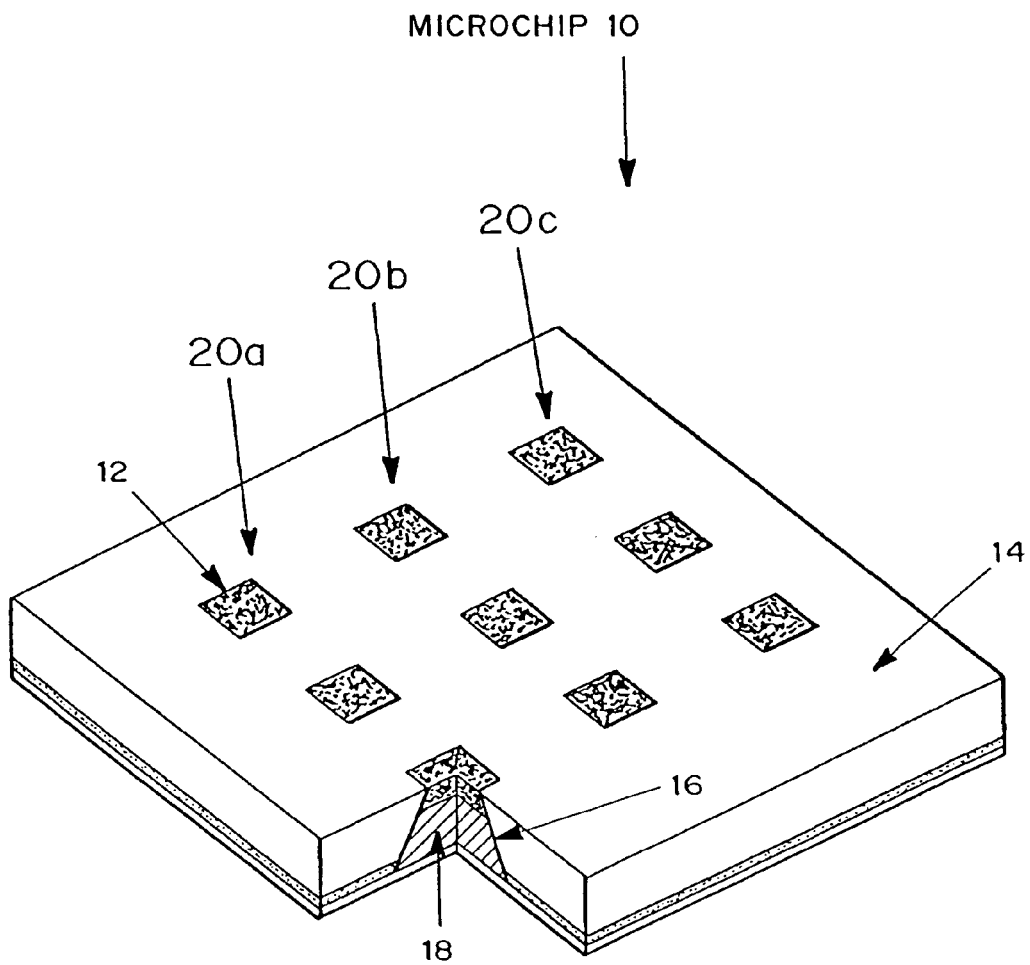
FIG. 4 depicts a passive delivery device.

A passive timed release device, microchip 10 is shown in FIG. 4. Microchip 10 is formed from substrate 14. Reservoirs 16 are etched into substrate 14. Positioned in reservoirs 16 is a release system containing molecules for delivery 18. The reservoirs are capped with reservoir caps 12. The release system and the molecules for delivery 18 can vary between rows 20a, 20b, 20c, and within reservoirs of each row.

Microchip 10 can be inserted into solution for in vitro applications or be implanted in a selected part of the body for in vivo applications and left to operate without requiring further attention. When exposed to the surrounding fluids, reservoir caps 12 will degrade or become permeable to the release system containing molecules for delivery 18.

EXAMPLE 4

Microchip With Active Controlled Time Release

Figure 5:
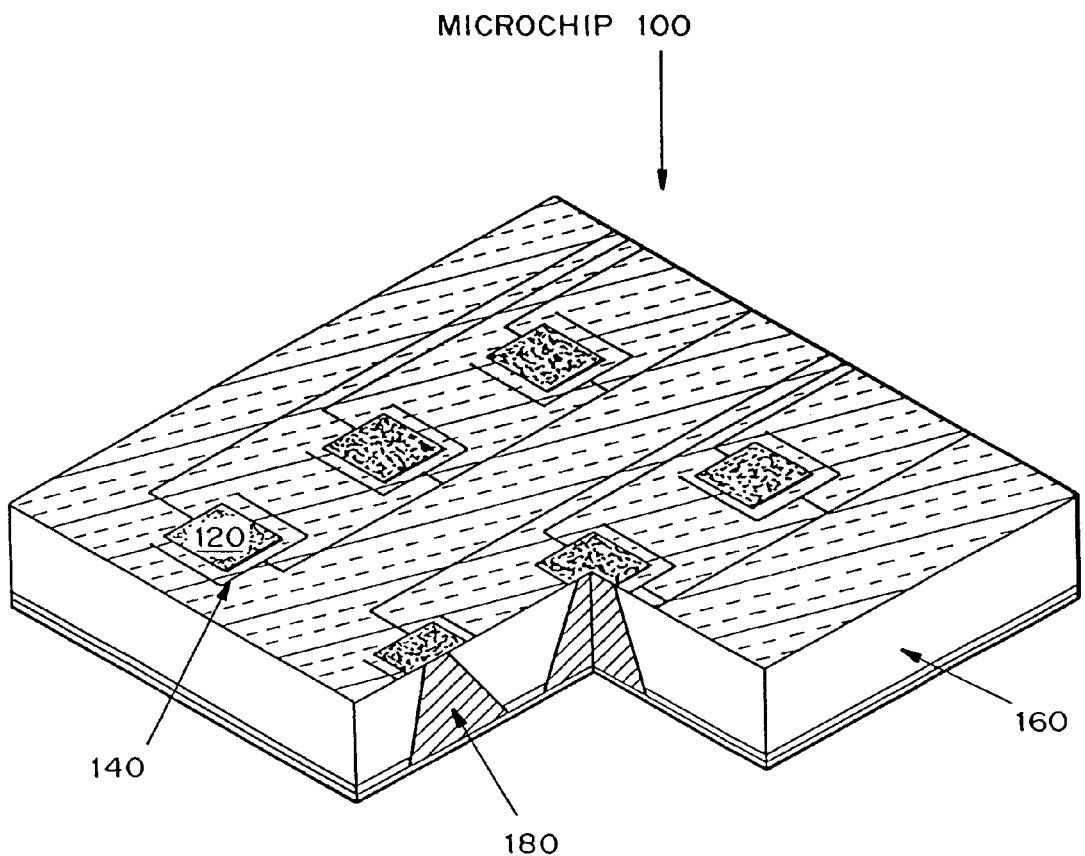
FIG. 5 depicts an active delivery device.

A drug delivery device that provides active timed release is shown as microchip 100 in FIG. 5. Microchip 100 is similar to microchip 10 except that microchip 100 contains electrodes that provide for active timed release. Microchip 100 is formed from substrate 160, release system containing molecules for delivery 180, anode reservoir caps 120, and cathodes 140. Preferably, microchip 100 further includes an input source, a microprocessor, a timer, a demultiplexer, and a power source (not shown). The power source provides energy to drive the reaction between selected anodes and cathodes. Upon application of a small potential between the electrodes, electrons pass from the anode to the cathode through the external circuit causing the anode material to oxidize and dissolve into the surrounding fluids, exposing the release system containing the molecules for delivery 180 to the surrounding fluids. The microprocessor directs power to specific electrode pairs through a demultiplexer as directed by a PROM, remote control, or biosensor.

Figure 6:
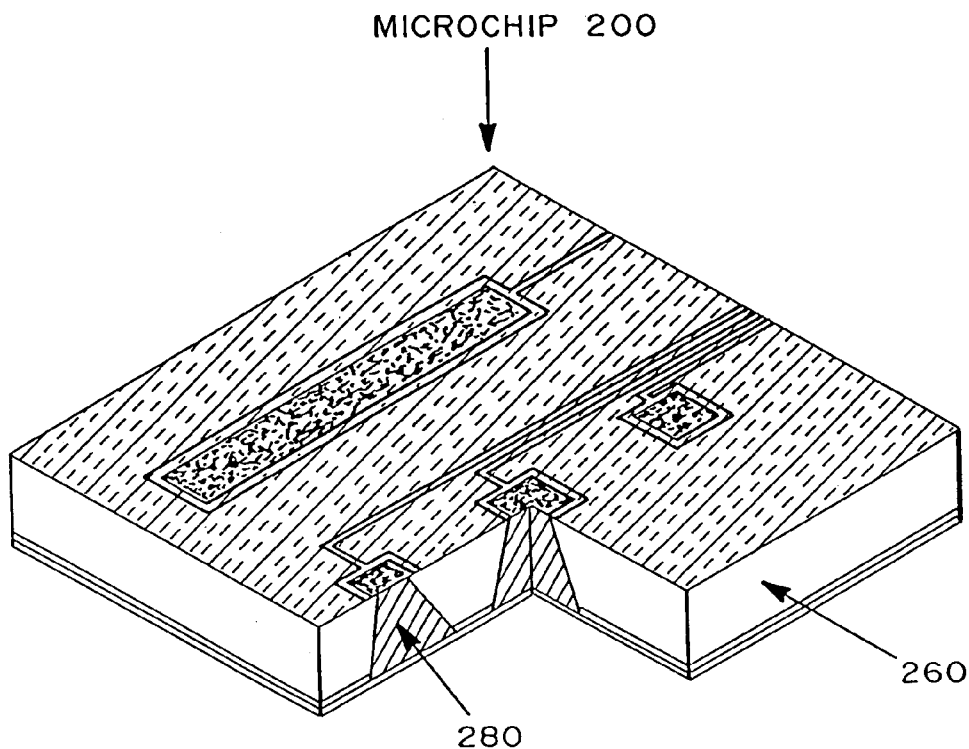
FIG. 6 depicts an active device including insulator overlayers.
Figure 7A:
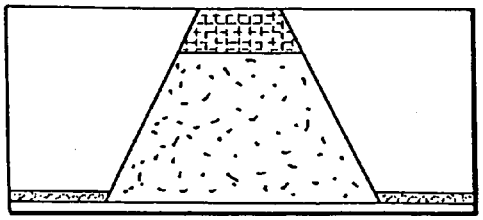
FIGS. 7a-i are schematic views of several configurations of passive delivery devices.
Figure 7E:
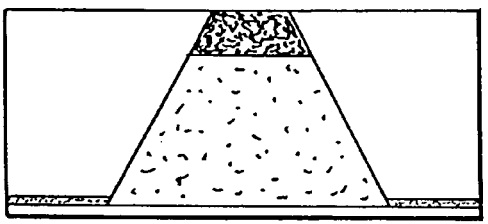
Figure 7B:
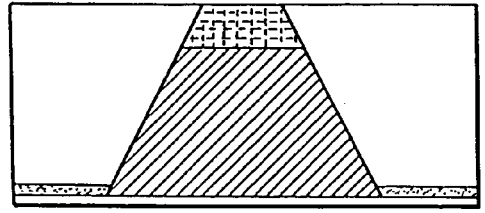
Figure 7F:
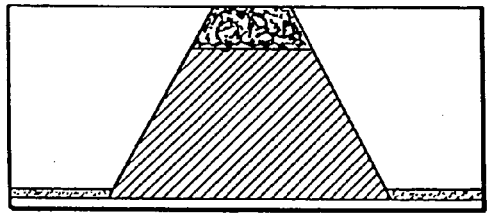
Figure 7C:
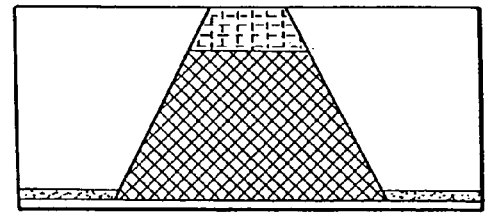
Figure 7G:
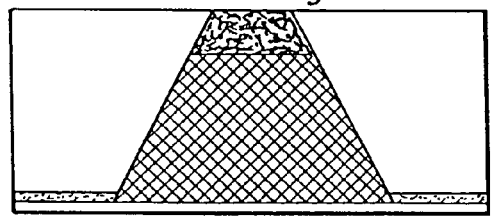
Figure 7D:
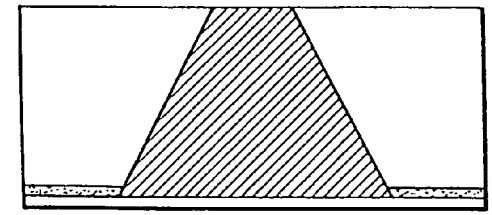
Figure 7H:
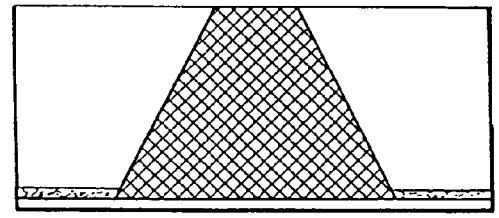
Figure 7I:
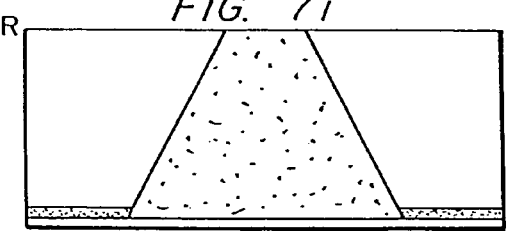

Another drug delivery device that provides active timed release is shown as microchip 200 in FIG. 6. Microchip 200, which includes substrate 260 and release system containing molecules 280 for delivery, is similar to microchip 100, but includes different electrode configurations. Microchip 200 illustrates that the shape, size, ratio, and placement of the anodes and cathodes can vary.

EXAMPLE 5

Microchip Device Having Multi-Portion Substrate

FIGS. 9a-e illustrate several typical variations of the devices wherein two or more substrate portions are attached to one another to form, for example, a larger or composite substrate. The reservoir caps are shown generically, that is, insulator/etch mask materials, insulator overlayer materials, and anode/cathode materials are omitted from these Figures, except where a specific embodiment is otherwise indicated. These devices can provide active release, passive release, or a combination thereof.

FIG. 9a, for comparison, shows a "single" substrate device 500, which has substrate 510, in which reservoirs 520 are filled with molecules to be released 540. Reservoirs 520 are covered by reservoir caps 530 and sealed with backing plate 550 or other type of seal.

FIG. 9b shows device 600 having a substrate formed of a top substrate portion 610a bonded to bottom substrate portion 610b. Reservoirs 620a, in top substrate portion 610a are in communication with reservoirs 620b in bottom substrate portion 610b. Reservoirs 620a/620b are filled with molecules to be released 640 and are covered by reservoir caps 630 and sealed with backing plate 650 or other type of seal.

FIG. 9c shows device 700 having a substrate formed of a top substrate portion 710a bonded to bottom substrate portion 710b. Top substrate portion 710a has reservoir 720a which is in communication with reservoir 720b in bottom substrate portion 710b. Reservoir 720b is much larger than reservoir 720a and reservoirs 720a/720b contain molecules to be released 740. Reservoirs 720a/720b are filled with molecules to be released 740 and are covered by reservoir cap 730 and sealed with backing plate 750 or other type of seal.

FIG. 9d shows device 800 having a substrate formed of a top substrate portion 810a bonded to bottom substrate portion 810b. Top substrate portion 810a has reservoir 820a which contains first molecules to be released 840a. Bottom substrate portion 810b has reservoir 820b which contains second molecules to be released 840b. First molecules to be released 840a can be the same or different from second molecules to be released 840b. Reservoir 820a is covered by reservoir cap 830a and sealed by reservoir cap 830b (formed of an anode material) and partially by bottom substrate portion 810b. Reservoir 820b is covered by internal reservoir cap 830b and sealed with backing plate 850 or other type of seal. Cathodes 860a and 860b are positioned to form an electric potential with anode reservoir cap 830b.

In one embodiment of the device shown in FIG. 9d, second molecules to be released 840b are first released from reservoir 820b, through or following the disintegration of reservoir cap 830b, into reservoir 820a, wherein the second molecules mix with first molecules to be released 840a before the mixture of molecules is released from reservoir 820a through or following the disintegration of reservoir cap 830a.

FIG. 9e simply shows another reservoir shape configuration in cross-section. Substrate portions 610a/710a/810a can be formed from the same or different materials and can have the same or different thicknesses as substrate portions 610b/710b/810b. These substrate portions can be bonded or attached together (as described in section IIA above) after they have been individually processed (e.g., etched), or they may be formed before they have any reservoirs or other features etched or micro-machined into them (such as in SOI substrates).

Modifications and variations of the methods and devices described herein will be obvious to those skilled in the art from the foregoing detailed description. Such modifications and variations are intended to come within the scope of the appended claims.

We claim:

1. A method for local delivery of drug molecules in a patient, the method comprising:
   implanting at a site in a patient a drug delivery device which comprises a support structure, at least two discrete reservoirs provided in spaced positions across at least one surface of the support structure, and a release system loaded in each of the reservoirs, the release system including drug molecules dispersed in a degradable matrix material; and
   allowing the matrix material to disintegrate in vivo to release the drug molecules from the reservoirs to the site in a controlled manner.

2. The method of claim 1, wherein the drug delivery device is implanted via a catheter.

3. The method of claim 1, wherein the drug molecules are released from the device in a pulsatile manner.

4. The method of claim 1, wherein the drug molecules are released from the device over a period of time of at least three months.

5. The method of claim 1, wherein one of the at least two reservoirs comprises two or more layers of the release system.

6. The method of claim 1, wherein the kinetics of release of the drug molecules from one of the at least two reservoirs is different than the kinetics of release of the drug molecules from the other of the at least two reservoirs.

7. The method of claim 1, wherein the drug delivery device further comprises at least two discrete degradable reservoir caps, each reservoir cap covering one of the at least two reservoirs and delaying onset of release of the drug molecules therefrom.

8. The method of claim 1, wherein the matrix material comprises a biodegradable or bioerodible polymeric material.

9. The method of claim 1, wherein the drug molecules comprise anesthetics, vaccines, chemotherapeutic agents, metabolites, immunomodulators, antioxidants, antibiotics, and ion channel regulators, or hormones.

10. The method of claim 1, wherein the substrate comprises silicon or metal.

11. The method of claim 1, wherein the substrate comprises a polymer.

12. The method of claim 1, wherein the reservoirs are microfabricated.

13. A method for local delivery drug molecules in a patient, the method comprising:
   implanting at a site in a patient a drug delivery device which comprises a support structure, at least two discrete reservoirs provided in spaced positions across at least one surface of the support structure, and a release system loaded in each of the reservoirs, the release system including drug molecules dispersed in a non-degradable matrix material; and
   allowing the drug molecules to diffuse from the matrix material in vivo to release the drug molecules from the reservoirs to the site in a controlled manner.

14. The method of claim 13, wherein the drug delivery device is implanted via a catheter.

15. The method of claim 13, wherein the drug molecules are released from the device over a period of time of at least three months.

16. The method of claim 13, wherein the kinetics of release of the drug molecules from one of the at least two reservoirs is different than the kinetics of release of the drug molecules from the other of the at least two reservoirs.

17. The method of claim 13, wherein the drug delivery device further comprises at least two discrete reservoir caps, each reservoir cap covering one of the at least two reservoirs and delaying the onset of release of the drug molecules therefrom.

18. The method of claim 17, wherein the reservoirs caps comprise a polymer.

19. The method of claim 13, wherein the matrix material comprises a polymeric material.

20. The method of claim 13, wherein the drug molecules comprise anesthetics, vaccines, chemotherapeutic agents, metabolites, immunomodulators, antioxidants, antibiotics, and ion channel regulators, or hormones.

21. The method of claim 13, wherein the substrate comprises silicon or metal.

22. The method of claim 13, wherein the substrate comprises a polymer.

23. The method of claim 13, wherein the reservoirs are microfabricated.

* * * * *